United States Patent
Koch et al.

(10) Patent No.: US 7,741,325 B2
(45) Date of Patent: Jun. 22, 2010

(54) **BENZO[*B*]CHROMENO-NAPHTHYRIDIN-7-ONE AND PYRANO[2',3':7,8]QUINO[2,3-*B*]QUINOXALIN-7-ONE COMPOUNDS**

(76) Inventors: Michel Koch, 116, Elysée II F, F-78170 La Celle Saint Cloud (FR); François Tillequin, 70, rue de l'Amiral Mouchez, F-75014 Paris (FR); Sylvie Michel, 3, rue Mandar, F-75002 Paris (FR); John Hickman, 126, boulevard Pereire, F-75017 Paris (FR); Alain Pierre, 9, Chemin des Bois Janeaudes, F-78580 Les Alluets le Roi (FR); Stéphane Leonce, 28 B, rue Henri Simon, F-78000 Versailles (FR); Bruno Pfeiffer, 47, rue Ernest Renan, F-95320 Saint Leu la Foret (FR); Pierre Renard, 3, avenue du Parc, F-78150 Le Chesnay (FR)

( * ) Notice: Subject to any disclaimer, the term of this patent is extended or adjusted under 35 U.S.C. 154(b) by 863 days.

(21) Appl. No.: 11/047,259

(22) Filed: Jan. 31, 2005

(65) Prior Publication Data
US 2005/0171114 A1 Aug. 4, 2005

(30) Foreign Application Priority Data
Feb. 3, 2004 (FR) .................................. 04 00988

(51) Int. Cl.
| | |
|---|---|
| A01N 43/58 | (2006.01) |
| A01N 43/60 | (2006.01) |
| A01N 43/42 | (2006.01) |
| A61K 31/50 | (2006.01) |
| A61K 31/495 | (2006.01) |
| A61K 31/44 | (2006.01) |
| C07D 241/36 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |

(52) U.S. Cl. ....................... 514/249; 514/283; 544/342; 546/48

(58) Field of Classification Search ............ None
See application file for complete search history.

(56) References Cited

U.S. PATENT DOCUMENTS 6,288,073 B1 * 9/2001 Koch et al. .................. 514/279

OTHER PUBLICATIONS

The Cecil reference (Cecil Textbook of Medicine, 21st Edition (2000), Goldman & Bennett (Editors), W.B. Saunders Company (Publisher), Chapter 198, pp. 1060-1074).*

Internal Medicine, 4th Edition, Editor-in-Chief Jay Stein, Chapters 71-72, pp. 699-715.*
Dorwald F. A. Side Reactions in Organic Synthesis, 2005, Wiley: VCH, Weinheim p. IX of Preface.*
http://www.fzi.uni-freiburg.de/InsectPestKey-long%20version/hemipter.htm, last accessed on Jun. 16, 2008.*
David-Cordonnier, et. al., Bioorganic & Medicinal Chemistry (2004), 12(1), 23-29.*

* cited by examiner

Primary Examiner—James O Wilson
Assistant Examiner—Jeffrey H Murray
(74) Attorney, Agent, or Firm—Hueschen and Sage

(57) ABSTRACT

A compound selected from those of formula (I):

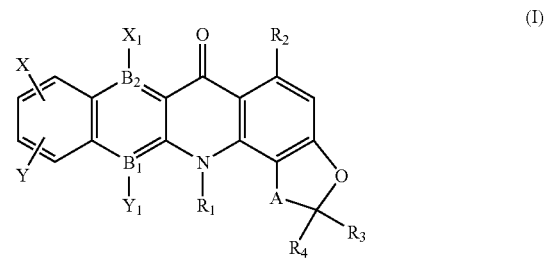

wherein:
$B_1$, $B_2$ represent carbon or nitrogen,

X, Y, $X_1$ and $Y_1$ represent a group selected from hydrogen, halogen, hydroxy, alkoxy, nitro, cyano, trihaloalkyl and $NR_aR_b$ wherein $R_a$ and $R_b$ are as defined in the description, $R_1$ represents hydrogen or alkyl, $R_2$ represents a group selected from hydrogen, alkyl, —OR"$_a$, —NR'$_a$R'$_b$, —O-$T_a$-OR"$_a$, —NR"$_a$-$T_a$-NR'$_a$R'$_b$, NR"$_a$—C(O)-$T_a$H, —O—C(O)-$T_a$H, —O-$T_a$-NR'$_a$R'$_b$', —NR"$_a$-$T_a$-OR"$_a$, —NR"$_a$-$T_a$-CO$_2$R"$_a$ and —NR"$_a$—C(O)-$T_a$-NR'$_a$R'$_b$ wherein R'$_a$, R'$_b$, R"$_a$ and $T_a$ are as defined in the description, $R_3$, $R_4$ represent hydrogen or alkyl, A represents a group of formula —CH($R_5$)—CH($R_6$)—, —CH═C($R_7$)—, —C($R_7$)═CH—, —C(O)—CH($R_8$)— or —CH($R_8$)—C(O)— wherein $R_5$, $R_6$, $R_7$ and $R_8$ are as defined in the description, its isomers, N-oxides, and addition salts thereof with a pharmaceutically acceptable acid or base, and medicinal products containing the same which are useful in the treatment of cancer.

19 Claims, No Drawings

BENZO[B]CHROMENO-NAPHTHYRIDIN-7-ONE AND PYRANO[2',3':7,8]QUINO[2,3-B] QUINOXALIN-7-ONE COMPOUNDS

FIELD OF THE INVENTION

The compounds of the invention are derivatives of acronycin, which is an alkaloid having anti-tumour properties that have been demonstrated in experimental models (*J. Pharm. Sci.*, 1966, 55 (8), 758-768). Despite having a broad spectrum of activity, however, acronycin is not very powerful and is only moderately active. In addition, this product is of low solubility, which limits its bioavailability and thus its use in pharmaceutical compositions administrable by the intravenous route.

Various modifications have been made to that molecule, such as those described in *J. Med. Chem.*, 1996, 39, 4762-4766, EP 1 042 326, EP 1 061 081 or EP 1 297 835, which have enabled significant improvement of the potency, the anti-tumour efficacy and the solubility of those products. Nevertheless, anti-cancer therapeutic requirements call for the constant development of new anti-tumour agents, with the aim of obtaining medicaments that are both more active and better tolerated. More especially, solid tumours pose a major problem for anti-cancer chemotherapy in view of their intrinsic and/or acquired resistance to existing products. It is accordingly of the utmost importance to have access to as broad as possible a range of products that express a strong cytotoxic activity in order to be able to have available the most effective treatments for tumour diseases as a whole.

In addition to the fact that the compounds of the invention are new, they have a surprising in vitro and in vivo cytotoxic activity superior to that observed hitherto. Thus, the compounds discovered by the Applicant have anti-tumour properties that make them particularly useful in the treatment of cancers. Among the types of cancer that can be treated by the compounds of the present invention, adenocarcinomas and carcinomas, sarcomas, gliomas and leukaemias may be mentioned without implying any limitation.

DETAILED DESCRIPTION OF THE INVENTION

More especially, the present invention relates to compounds of formula (I):

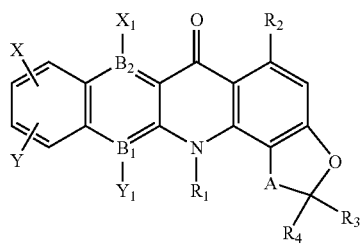

(I)

wherein:

$B_1$ and $B_2$, which may be identical or different, each independently of the other represents a carbon atom or a nitrogen atom, with the proviso that at least one of the two groups $B_1$ or $B_2$ represents a nitrogen atom, X and Y, which may be identical or different, each independently of the other represents one or more groups selected from:

the atoms hydrogen and halogen, the groups hydroxy, linear or branched ($C_1$-$C_6$)alkoxy, nitro, cyano, linear or branched ($C_1$-$C_6$)alkyl, linear or branched ($C_2$-$C_6$)alkenyl, linear or branched ($C_1$-$C_6$)-polyhaloalkyl, or groups of formula —$NR_aR_b$ wherein:

$R_a$ and $R_b$, which may be identical or different, each independently of the other represents a group selected from hydrogen and the groups —C(O)—$CF_3$, —C(O)—$NH_2$ and linear or branched ($C_1$-$C_6$)alkyl, optionally substituted by a group $NR'_aR'_b$ wherein:

$R'_a$ and $R'_b$, which may be identical or different, each independently of the other represents a group selected from hydrogen and linear or branched ($C_1$-$C_6$)alkyl, or $R'_a$ and $R'_b$, together with the nitrogen atom carrying them, form a monocyclic heterocycle having from 5 to 7 ring members and optionally containing in the ring system a second hetero atom selected from oxygen and nitrogen, or $R_a$ and $R_b$, together with the nitrogen atom carrying them, form a monocyclic heterocycle having from 5 to 7 ring members and optionally containing in the ring system a second hetero atom selected from oxygen and nitrogen, $X_1$ and $Y_1$, which may be identical or different, each independently of the other represents a group selected from the substituents as defined for X and Y, it being understood that, when $B_1$ and/or $B_2$ represent a nitrogen atom, $B_1$ and $B_2$ do not carry substituents $Y_1$ and $X_1$ respectively, $R_1$ represents a hydrogen atom or a linear or branched ($C_1$-$C_6$)alkyl group, $R_2$ represents a group selected from hydrogen and the groups linear or branched ($C_1$-$C_6$)alkyl, —$OR''_a$; —$NR'_aR'_b$; —O-$T_a$-$OR''_a$; —$NR''_a$-$T_a$-$NR'_aR'_b$; —$NR''_a$—C(O)-$T_a$H; O—C(O)-$T_a$H; —O-$T_a$-$NR'_aR'_b$; —$NR''_a$-$T_a$-$OR''_a$; —$NR''_a$-$T_a$-$CO_2R''_a$; and —$NR''_a$—C(O)-$T_a$-$NR'_aR'_b$, wherein:

$T_a$ represents a linear or branched ($C_1$-$C_6$)alkylene chain, $R'_a$ and $R'_b$ are as defined hereinbefore, $R''_a$ represents a group selected from hydrogen and linear or branched ($C_1$-$C_6$)alkyl, $R_3$ and $R_4$, which may be identical or different, each independently of the other represents a hydrogen atom or a linear or branched ($C_1$-$C_6$)alkyl group, or $R_3$ and $R_4$, together with the carbon atom carrying them, form a monocyclic ring having from 3 to 6 ring members, A represents a group of formula:

—CH($R_5$)—CH($R_6$)— wherein: a)

$R_5$ and $R_6$, which may be identical or different, each represents independently of the other a group selected from:

1) hydrogen,
2) the groups $OR_c$, $NR_cR_d$, $SR_c$, wherein:

$R_c$, $R_d$, which may be identical or different, each independently of the other represents a group selected from hydrogen, the groups linear or branched ($C_1$-$C_6$) alkyl, aryl and aryl-($C_1$-$C_6$)alkyl in which the alkyl moiety may be linear or branched, or the group C(O)—$R_e$ wherein $R_e$ represents a group selected from hydrogen, aryl or $NR'''_aR'''_b$ wherein $R'''_a$ and $R'''_b$ are identical and represent a hydrogen atom or wherein $R'''_a$ and $R'''_b$, together with the nitrogen atom carrying them, form a monocyclic heterocycle having from 5 to 7 ring members and optionally containing in the ring system a second hetero atom selected from oxygen and nitrogen, 3) $W_1$—$C(W_2)$—U—V wherein:
   α) $W_1$ represents an oxygen atom, a sulphur atom or $NR_c$ (wherein $R_c$ is as defined hereinbefore),
   β) $W_2$ represents an oxygen atom or a sulphur atom,
   γ) U represents a linear or branched ($C_1$-$C_8$)alkylene chain or a linear or branched ($C_2$-$C_8$)alkenylene chain,
   δ) V represents a group selected from
   hydrogen,
   aryl,
   and the groups $OR_c$, $CO_2R_c$, $COR_c$, $CONR'_aR'_b$, $NR_cR_d$, $N(R_c)$—$CO_2R'_c$, $N(R_c)$—$COR'_c$, wherein $R'_a$, $R'_b$, $R_c$ and $R_d$ are as defined hereinbefore and $R'_c$ represents a group selected from hydrogen, linear or branched ($C_1$-$C_6$)alkyl, aryl, or aryl-($C_1$-$C_6$)alkyl in which the alkyl moiety may be linear or branched,
   ε) U represents a bond when $W_2$ does not represent an oxygen atom and when V does not represent a group selected from:
   hydrogen
   aryl and
   $NH_2$, 4) $W_1$—$C(W_2)$—$W_3$-$T_1$ wherein:
   α) $W_1$ and $W_2$ are as defined hereinbefore,
   β) $W_3$ represents an oxygen atom, a sulphur atom, or $NR_c$ wherein $R_c$ is as defined hereinbefore,
   γ) $T_1$ represents a group selected from:
   hydrogen,
   linear or branched ($C_1$-$C_6$)alkyl,
   linear or branched ($C_2$-$C_6$)alkenyl,
   aryl, aryl-($C_1$-$C_6$)alkyl in which the alkyl moiety may be linear or branched, and
   linear or branched ($C_1$-$C_6$)alkylene or linear or branched ($C_2$-$C_6$)alkenylene chains, each of which is substituted by a group $OR_c$ wherein $R_c$ is as defined hereinbefore or $NR'_aR'_b$ wherein $R'_a$ and $R'_b$ are as defined hereinbefore, 5) $W_1$—$S(O)_n$—$W_3$-$T_1$ wherein:
   α) $W_1$, $W_3$ and $T_1$ are as defined hereinbefore, and
   β) n represents an integer selected from 1 and 2, 6) $W_1$—$S(O)_n$-$T_1$ wherein $W_1$, $T_1$ and n are as defined hereinbefore, and 7) $C(W_2)$-$T_1$ wherein $W_2$ and $T_1$ are as defined hereinbefore, or $R_5$ and $R_6$, together form:

1) a group

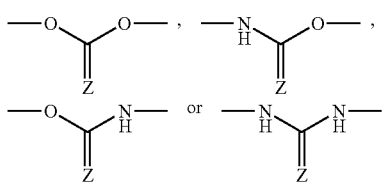

wherein Z represents an oxygen atom or a sulphur atom, 2) a group -O—$(CH_2)_m$—O— wherein m represents an integer of from 1 to 4 inclusive, or 3) a group

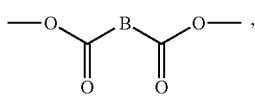

-continued

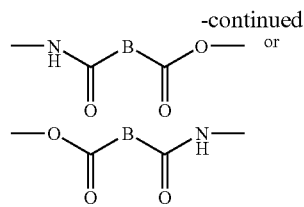

wherein B represents a single bond, a linear or branched ($C_1$-$C_6$)alkylene chain or a linear or branched ($C_2$-$C_6$) alkenylene chain,
   or $R_5$ and $R_6$, together with the carbon atoms carrying them, form an oxirane group or an aziridine group, optionally substituted on the nitrogen atom by a linear or branched ($C_1$-$C_6$)alkyl group, b) —CH═$C(R_7)$— or —$C(R_7)$═CH— wherein $R_7$ represents a group selected from:
   hydrogen,
   and the groups $OR''_a$, $W_1$—$C(W_2)$—U—V, $W_1$—C$(W_2)$—$W_3$-$T_1$, $W_1$—$S(O)_n$—$W_3$-$T_1$, $W_1$—$S(O)_n$-$T_1$ and $C(W_2)$-$T_1$ wherein $R''_a$, $W_1$, $W_2$, U, V, $W_3$, $T_1$ and n are as defined hereinbefore, or c) —C(O)—$CH(R_8)$— or —$CH(R_8)$—C(O)— wherein $R_8$ represents a group selected from:
   hydrogen,
   linear or branched ($C_1$-$C_6$)alkylcarbonyloxy and the groups $OR''_1$ wherein $R''_a$ is as defined hereinbefore, to their enantiomers, diastereoisomers, N-oxides, and also to addition salts thereof with a pharmaceutically acceptable acid or base, wherein aryl is understood as a phenyl or naphthyl group optionally containing one or more identical or different substituents selected from linear or branched ($C_1$-$C_6$)alkyl, linear or branched ($C_2$-$C_6$)alkenyl, hydroxy, halogen, carboxy, nitro, amino, alkylamino or dialkylamino in which the alkyl moieties contain from 1 to 6 carbon atoms and may be linear or branched, linear or branched ($C_1$-$C_6$)alkoxy, linear or branched ($C_1$-$C_6$)acyl and linear or branched ($C_1$-$C_6$)alkylcarbonyloxy, among the monocyclic heterocycles having from 5 to 7 ring members and optionally containing in the ring system a second hetero atom selected from oxygen and nitrogen there may be mentioned, without implying any limitation, the groups pyrrolidinyl, isoxazolidinyl, oxazolidinyl, pyrazolidinyl, imidazolidinyl, piperidyl, morpholinyl, hexahydropyridazinyl, hexahydropyrimidinyl, piperazinyl, azepanyl, oxazepanyl and diazepanyl, among the monocyclic rings having from 3 to 6 ring members there may be mentioned, without implying any limitation, the groups cyclopropyl, cyclobutyl, cyclopentyl and cyclohexyl.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, lysine etc. . . .

Among the pharmaceutically acceptable bases there may be mentioned, without implying any limitation, sodium hydroxide, potassium hydroxide, triethylamine, tert-butylamine, etc. . . .

According to an advantageous embodiment of the invention, preferred compounds are those of formula (IA):

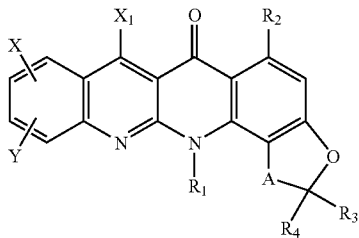

(IA)

wherein X, Y, $X_1$, $R_1$, $R_2$, $R_3$, $R_4$ and A are as defined for formula (I).

According to a second advantageous embodiment of the invention, preferred compounds are those of formula (IB):

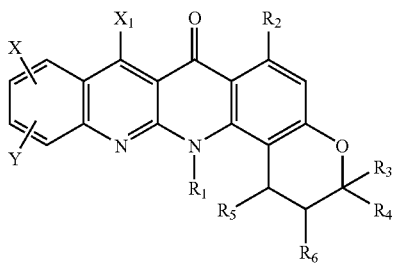

(IB)

wherein X, Y, $X_1$, $R_1$, $R_2$, $R_3$, $R_4$, $R_5$ and $R_6$ are as defined for formula (I).

According to a third advantageous embodiment of the invention, preferred compounds are those of formula (IC):

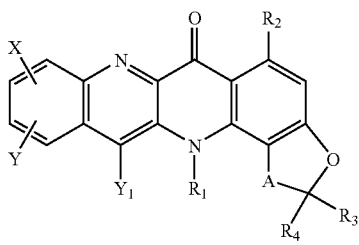

(IC)

wherein X, Y, $Y_1$, $R_1$, $R_2$, $R_3$, $R_4$ and A are as defined for formula (I).

According to a fourth advantageous embodiment of the invention, preferred compounds are those of formula (ID):

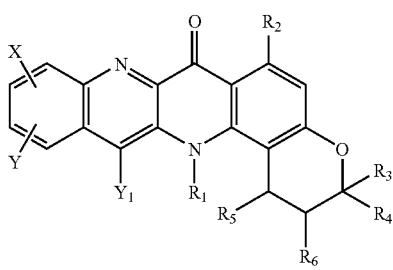

(ID)

wherein X, Y, $Y_1$, $R_1$, $R_2$, $R_3$, $R_4$, $R_5$ and $R_6$ are as defined for formula (I).

According to a fifth advantageous embodiment of the invention, preferred compounds are those of formula (IE):

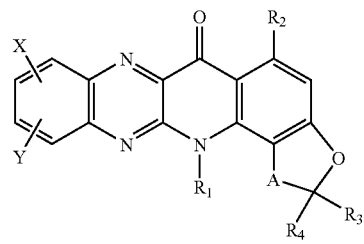

(IE)

wherein X, Y, $R_1$, $R_2$, $R_3$, $R_4$ and A are as defined for formula (I).

According to a sixth advantageous embodiment of the invention, preferred compounds are those of formula (IF):

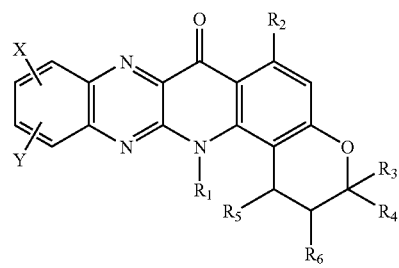

(IF)

wherein X, Y, $R_1$, $R_2$, $R_3$, $R_4$, $R_5$ and $R_6$ are as defined for formula (I).

Preferred compounds of formulae (IB), (ID) and (IF) are those wherein $R_5$ and $R_6$ are identical and represent a group of formula —$OR_c$ or $W_1$—C($W_2$)—U—V or wherein $R_5$ and $R_6$ together form a group

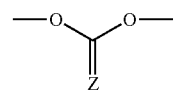

wherein $R_c$, $W_1$, $W_2$, U, V and Z are as defined for formula (I).

Of particular interest, preferred compounds of formula (IB), (ID) and (IF) are those wherein $R_5$ and $R_6$ are identical and represent a group of formula —$OR_c$ wherein $R_c$ represents a hydrogen atom or a linear or branched ($C_1$-$C_6$)alkyl group.

Also of particular interest, preferred compounds of formulae (IB), (ID) and (IF) are those wherein $R_5$ and $R_6$ are identical and represent a group of formula $W_1$—C($W_2$)—U—V wherein $W_1$ and $W_2$ represent an oxygen atom, U represents a linear or branched ($C_1$-$C_6$)alkylene chain and V represents a hydrogen atom.

Also of very particular interest, preferred compounds of formulae (IB), (ID) and (IF) are those wherein $R_5$ and $R_6$ together form a group

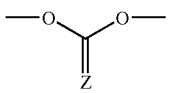

wherein Z represents an oxygen atom.

According to a seventh advantageous embodiment of the invention, preferred compounds are those of formula (IG):

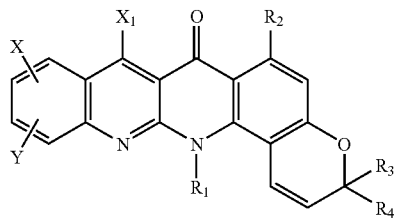

(IG)

wherein X, Y, X$_1$, R$_1$, R$_2$, R$_3$ and R$_4$ are as defined for formula (I).

According to an eighth advantageous embodiment of the invention, preferred compounds are those of formula (IH):

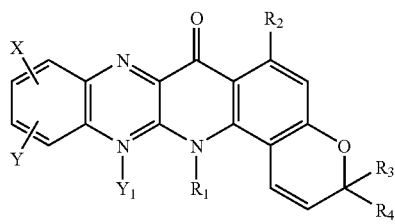

(IH)

wherein X, Y, Y$_1$, R$_1$, R$_2$, R$_3$ and R$_4$ are as defined for formula (I).

According to a ninth advantageous embodiment of the invention, preferred compounds are those of formula (IJ):

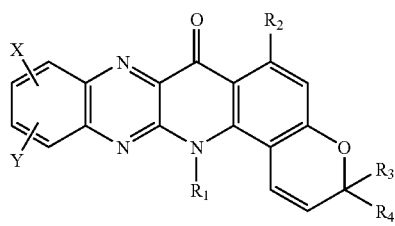

(IJ)

wherein X, Y, R$_1$, R$_2$, R$_3$ and R$_4$ are as defined for formula (I).

Substituents R$_3$ and R$_4$ preferred in accordance with the invention are linear or branched (C$_1$-C$_6$)alkyl groups.

The substituent R$_2$ preferred in accordance with the invention is the group —OR"$_a$ wherein R"$_a$ is as defined for formula (I).

Even more especially, the substituent R$_2$ preferred in accordance with the invention is the group —OR"$_a$ wherein R"$_a$ represents a linear or branched (C$_1$-C$_6$)alkyl group, and even more especially a methyl group.

Preferred in accordance with the invention as substituents X, Y, X$_1$ and Y$_1$ is hydrogen.

Especially advantageously, preferred compounds of the invention are the following:
- (±)-cis-1,2-dihydroxy-6-methoxy-3,3,14-trimethyl-1,2,3,14-tetrahydro-7H-benzo[b]-chromeno[6,5-g][1,8]naphthyridin-7-one,
- (±)-cis-1,2-diacetoxy-6-methoxy-3,3,14-trimethyl-1,2,3,14-tetrahydro-7H-benzo[b]-chromeno[6,5-g][1,8]naphthyridin-7-one,
- (±)-cis-7-methoxy-4,4,15-trimethyl-15,15c-dihydro-4H-benzo[b][1,3]dioxolo-[4',5':3,4]chromeno[6,5-g][1,8]naphthyridine-2,8(3aH)-dione, The enantiomers, diastereoisomers, N-oxides and addition salts with a pharmaceutically acceptable acid or base of the preferred compounds of the invention form an integral part of the invention.

The present invention relates also to a process for the preparation of compounds of formula (I), which is characterised in that there is used as starting material a compound of formula (II):

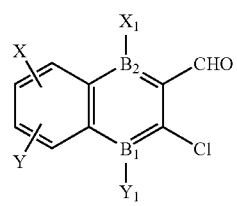

(II)

wherein X, Y, X$_1$, Y$_1$, B$_1$ and B$_2$ are as defined for formula (I), which compounds of formula (II) are placed in the presence of pyridinium dichromate to yield compounds of formula (III):

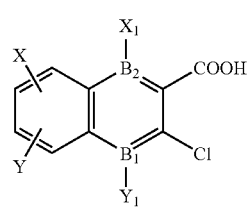

(III)

wherein X, Y, X$_1$, Y$_1$, B$_1$ and B$_2$ are as defined for formula (I), which compounds of formula (III) are treated in basic and anhydrous medium with a compound of formula (IV):

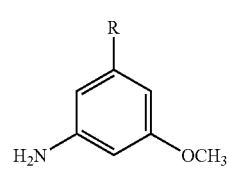

(IV)

wherein R represents a hydrogen atom, a hydroxy group, a linear or branched (C$_1$-C$_6$)alkyl group or a linear or branched (C$_1$-C$_6$)alkoxy group to yield compounds of formula (V):

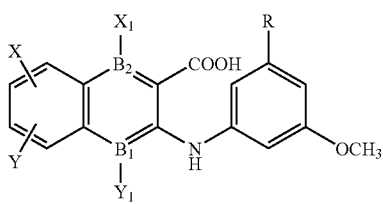

(V)

wherein X, Y, $X_1$, $Y_1$, $B_1$, $B_2$ and R are as defined for formula (I), which compounds of formula (V) are placed in the presence of polyphosphoric acid to yield compounds of formula (VI):

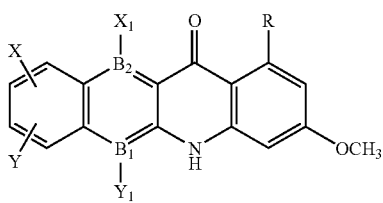

(VI)

wherein X, Y, $X_1$, $Y_1$, $B_1$, $B_2$ and R are as defined hereinbefore, of which compounds of formula (VI):

a) the nitrogen atom is substituted by the action of an alkyl halide or of a dialkyl sulphate in the presence of a deprotonation agent, in a polar aprotic solvent, to yield compounds of formula (VII):

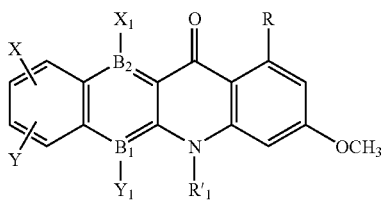

(VII)

wherein $R'_1$ represents a linear or branched $(C_1\text{-}C_6)$alkyl group and X, Y, $X_1$, $Y_1$, $B_1$, $B_2$ and R are as defined hereinbefore, which compounds of formula (VII) are treated with a solution of hydrobromic acid in acetic acid to yield compounds of formula (VIII):

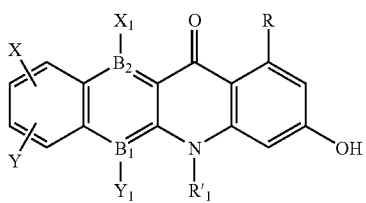

(VIII)

wherein X, Y, $X_1$, $Y_1$, $B_1$, $B_2$, R and $R'_1$ are as defined hereinbefore, which compounds of formula (VIII) are then treated under basic conditions, in an anhydrous aprotic solvent, with an alkyne of formula (IX):

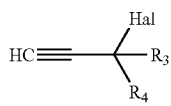

(IX)

wherein Hal represents a halogen atom and $R_3$ and $R_4$ are as defined for formula (I) to yield compounds of formula (X):

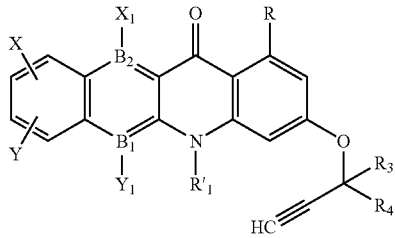

(X)

wherein X, Y, $X_1$, $Y_1$, $B_1$, $B_2$, R, $R'_1$, $R_3$ and $R_4$ are as defined hereinbefore, which compounds of formula (X) are refluxed in anhydrous dimethylformamide to yield compounds of formula (I/a), a particular case of the compounds of formula (I):

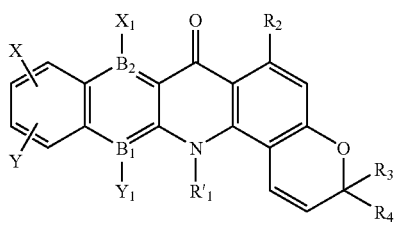

(I/a)

wherein X, Y, $X_1$, $Y_1$, $B_1$, $B_2$, R, $R'_1$, $R_3$ and $R_4$ are as defined hereinbefore, or which compounds of formula (VI)

b) are subjected to the same conditions as the compounds of formula (VII) to yield compounds of formula (XI):

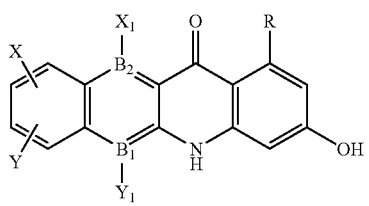

(XI)

wherein X, Y, $X_1$, $Y_1$, $B_1$, $B_2$ and R are as defined hereinbefore, which compounds of formula (XI) are subjected in succession to the same conditions as the compounds of formula (VIII) and (X) to yield compounds of formula (I/b), a particular case of the compounds of formula (I):

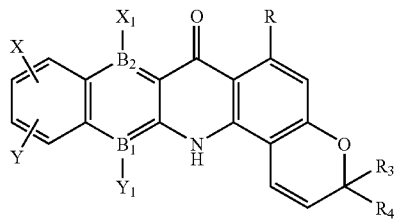

(I/b)

wherein X, Y, $X_1$, $Y_1$, $B_1$, $B_2$, R, $R_3$ and $R_4$ are as defined hereinbefore, the totality of the compounds (I/a) and (I/b) constituting the compounds of formula (I/c), a particular case of the compounds of formula (I):

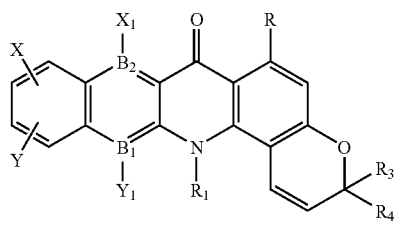

(I/c)

wherein $R_1$ is as defined for formula (I) and X, Y, $X_1$, $Y_1$, $B_1$, $B_2$, R, $R_3$ and $R_4$ are as defined hereinbefore, which compounds of formula (I/c) are, if desired, subjected to the action of an alkylating agent or an acylating agent to yield compounds of formula (I/d), a particular case of the compounds of formula (I):

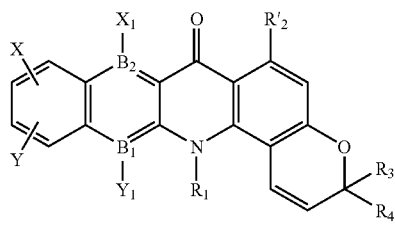

(I/d)

wherein X, Y, $X_1$, $Y_1$, $B_1$, $B_2$, $R_1$, $R_3$ and $R_4$ are as defined hereinbefore, and $R'_2$ represents a group selected from —OR"$_{a1}$, O-T$_a$-OR'$_a$, —O—C(O)-T$_a$H and —O-T$_a$-NR'$_a$R'$_b$ wherein R'$_a$, R'$_b$, R"$_a$ and T$_a$ are as defined for formula (I) and R"$_{a1}$ represents a linear or branched ($C_1$-$C_6$)alkyl group, which compounds of formula (I/d) are, if desired, treated, when $R'_2$ represents a group —OR"$_{a1}$ wherein R"$_{a1}$ is as defined hereinbefore, with a compound of formula (XII):

HNR$_{10}$R$_{11}$   (XII)

wherein $R_{10}$ represents a group selected from R'$_a$ and R"$_a$, and $R_{11}$ represents a group selected from R'$_b$, -T$_a$-NR'$_a$R'$_b$, —C(O)-T$_a$H, -T$_a$-OR"$_a$, -T$_a$-CO$_2$R"$_a$ and —C(O)-T$_a$-NR'$_a$R'$_b$ wherein R'$_a$, R'$_b$, R"$_a$ and T$_a$ are as defined hereinbefore, to yield compounds of formula (I/e), a particular case of the compounds of formula (I):

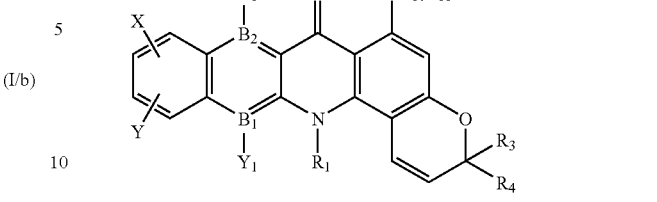

(I/e)

wherein X, Y, $X_1$, $Y_1$, $B_1$, $B_2$, $R_1$, $R_3$, $R_4$, $R_{10}$ and $R_{11}$ are as defined hereinbefore, the totality of the compounds of formulae (I/c), (I/d) and (I/e) constituting the compounds of formula (I/f), a particular case of the compounds of formula (I):

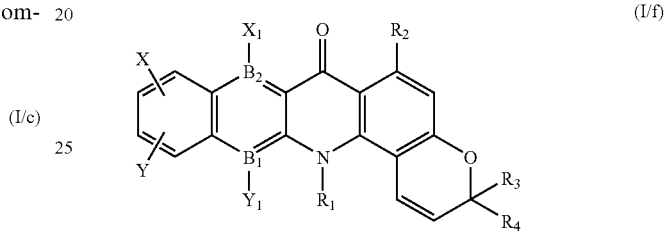

(I/f)

wherein X, Y, $X_1$, $Y_1$, $B_1$, $B_2$, $R_1$, $R_2$, $R_3$ and $R_4$ are as defined for formula (I), which compounds of formula (I/f) may be subjected,
a) either to the action of a reducing agent to yield compounds of formula (I/g), a particular case of the compounds of formula (I):

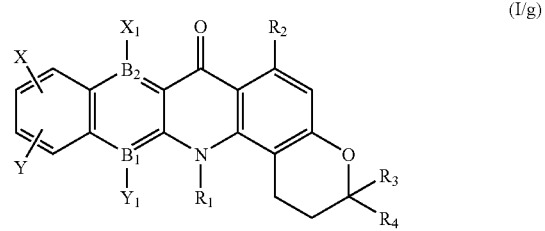

(I/g)

wherein X, Y, $X_1$, $Y_1$, $B_1$, $B_2$, $R_1$, $R_2$, $R_3$ and $R_4$ are as defined hereinbefore,
b) or to the action of osmium tetroxide in polar medium, and in the presence of 4-methylmorpholine-N-oxide, to yield compounds of formulae (I/h$_1$) and (I/h$_2$), a particular case of the compounds of formula (I):

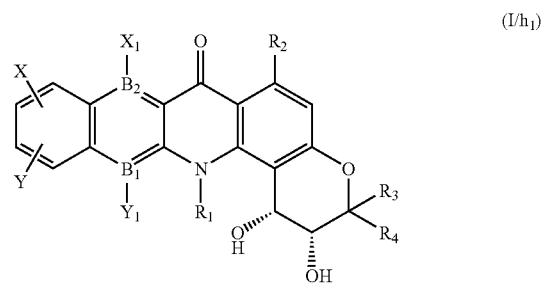

(I/h$_1$)

-continued

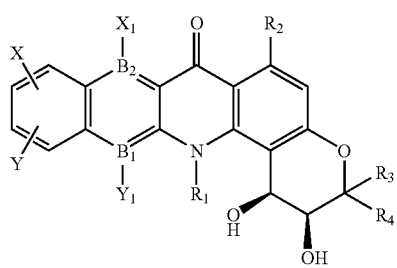
(I/h₂)

wherein X, Y, X₁, Y₁, B₁, B₂, R₁, R₂, R₃ and R₄ are as defined hereinbefore, the totality of the compounds of formulae (I/h₁) and (I/h₂) constituting the cis-diol compounds of formula (cis-I/h), a particular case of the compounds of formula (I):

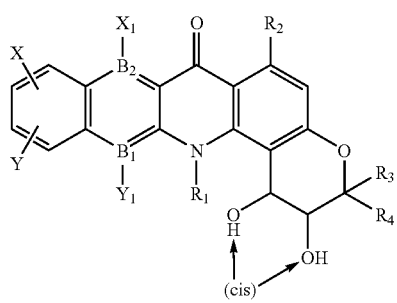
(cis-I/h)

wherein X, Y, X₁, Y₁, B₁, B₂, R₁, R₂, R₃ and R₄ are as defined hereinbefore, which cis-diol compounds of formula (cis-I/h) are optionally subjected to the action of a compound of formula (XIII):

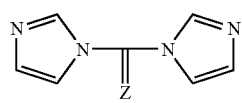
(XIII)

wherein Z is as defined for formula (I) to yield compounds of formula (cis-I/i), a particular case of the compounds of formula (I):

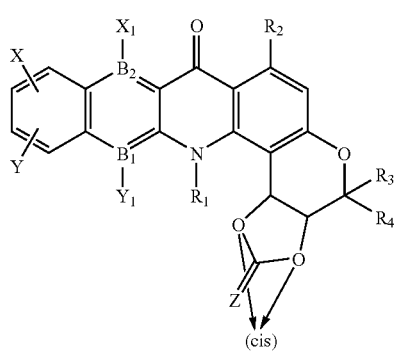
(cis-I/i)

wherein X, Y, X₁, Y₁, B₁, B₂, R₁, R₂, R₃ and R₄ are as defined hereinbefore, c) or to the action of potassium permanganate in polar medium to yield compounds of formula (I/j), a particular case of the compounds of formula (I):

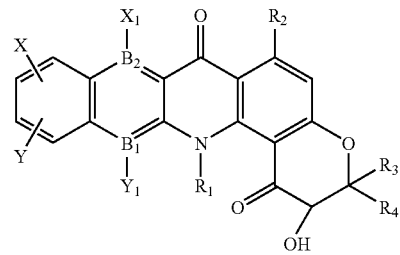
(I/j)

wherein X, Y, X₁, Y₁, B₁, B₂, R₁, R₂, R₃ and R₄ are as defined hereinbefore, which compounds of formula (I/j) may be subjected:

α) either to the action of an alkylating agent or an acylating agent to yield compounds of formula (I/k), a particular case of the compounds of formula (I):

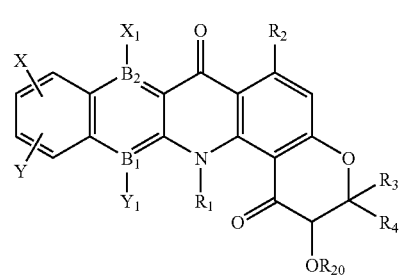
(I/k)

wherein X, Y, X₁, Y₁, B₁, B₂, R₁, R₂, R₃ and R₄ are as defined hereinbefore, and $R_{20}$ represents a group selected from linear or branched ($C_1$-$C_6$)alkyl and linear or branched ($C_1$-$C_6$) alkylcarbonyl, β) or to the action of a protecting group $P_G$ for the hydroxy function then to the action of $P_2S_5$ to yield compounds of formula (XIV):

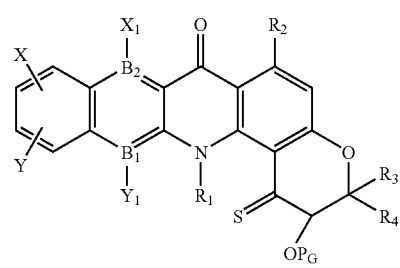
(XIV)

wherein X, Y, X₁, Y₁, B₁, B₂, R₁, R₂, R₃, R₄ and $P_G$ are as defined hereinbefore, which compounds of formula (XIV) are treated with a reducing agent, then subjected to a reaction for deprotection of the hydroxy function, to yield compounds of formula (I/l), a particular case of the compounds of formula (I):

(I/l)

wherein X, Y, X$_1$, Y$_1$, B$_1$, B$_2$, R$_1$, R$_2$, R$_3$ and R$_4$ are as defined hereinbefore, which compounds of formula (I/l) are, if desired, subjected to the action of a compound of formula (XV):

Hal-G  (XV)

wherein Hal represents a halogen atom and G$_1$ represents a group selected from —R$_c$, —C(W$_2$)—U—V, —C(W$_2$)—W$_3$-T$_1$, -S(O)$_n$—W$_3$-T$_1$ and —S(O)$_n$-T$_1$ wherein R$_c$, W$_2$, W$_3$, U, V, T$_1$ and n are as defined for formula (I) to yield compounds of formula (I/m), a particular case of the compounds of formula (I):

(I/m)

wherein X, Y, X$_1$, Y$_1$, B$_1$, B$_2$, R$_1$, R$_2$, R$_3$, R$_4$ and G$_1$ are as defined hereinbefore, which compounds of formula (I/m) may be subjected to the action of a compound of formula (XVI):

Hal-G'$_1$  (XVI)

wherein Hal is as defined hereinbefore and G'$_1$ represents a group selected from —R$_c$, —C(W$_2$)—U—V, —C(W$_2$)—W$_3$-T$_1$, -S(O)$_n$—W$_3$-T$_1$ and —S(O)$_n$-T$_1$ wherein R$_c$, W$_2$, W$_3$, U, V, T$_1$ and n are as defined for formula (I), to yield compounds of formula (I/n), a particular case of the compounds of formula (I):

(I/n)

wherein X, Y, X$_1$, Y$_1$, B$_1$, B$_2$, R$_1$, R$_2$, R$_3$, R$_4$, G$_1$ and G'$_1$ are as defined hereinbefore, γ) or to reducing conditions in the presence of NaBH$_4$ to yield compounds of formula (I/o), a particular case of the compounds of formula (I):

(I/o)

(trans)

wherein X, Y, X$_1$, Y$_1$, B$_1$, B$_2$, R$_1$, R$_2$, R$_3$ and R$_4$ are as defined hereinbefore, the totality of the compounds of formulae (cis-I/h) and (I/o) constituting the compounds of formula (I/p), (I/p)

wherein X, Y, X$_1$, Y$_1$, B$_1$, B$_2$, R$_1$, R$_2$, R$_3$ and R$_4$ are as defined hereinbefore, which compounds of formula (I/p) may be subjected:

α) either to the action of a compound of formula (XVI) as defined hereinbefore to yield compounds of formulae (I/q$_1$), (I/q$_2$) and (I/q$_3$), particular cases of the compounds of formula (I):

(I/q$_1$)

(I/q$_2$)

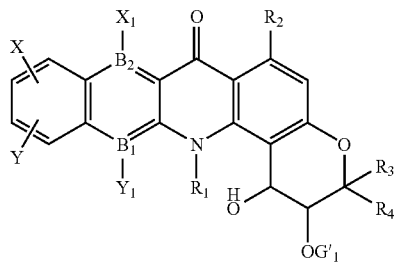
(I/q₃)

wherein X, Y, $X_1$, $Y_1$, $B_1$, $B_2$, $R_1$, $R_2$, $R_3$, $R_4$ and $G'_1$ are as defined hereinbefore, which compounds of formulae (I/q₂) and (I/q₃) are, if desired, subjected:

1) either to the action of an alcohol of formula $R_{30}$—OH wherein $R_{30}$ represents a linear or branched ($C_1$-$C_6$) alkyl group to yield, respectively, compounds of formulae (I/r₂) and (I/r₃), particular cases of the compounds of formula (I):

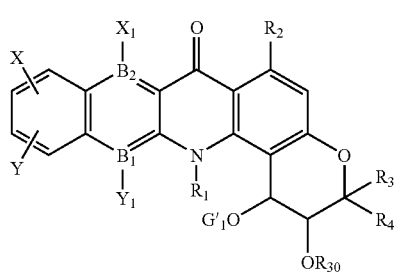
(I/r₂)

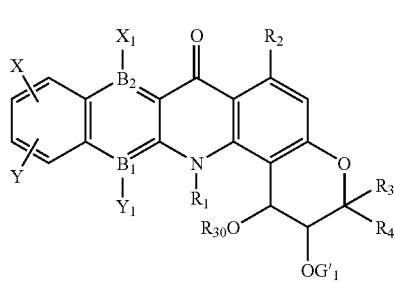
(I/r₃)

wherein X, Y, $X_1$, $Y_1$, $B_1$, $B_2$, $R_1$, $R_2$, $R_3$, $P_4$, $G'_1$ and $R_{30}$ are as defined hereinbefore, 2) or to the action of an anhydride of formula (XVII):

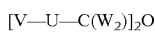   (XVII)

wherein $W_2$, U and V are as defined for formula (I) to yield compounds of formulae (I/s₂) and (I/s₃), particular cases of the compounds of formula (I):

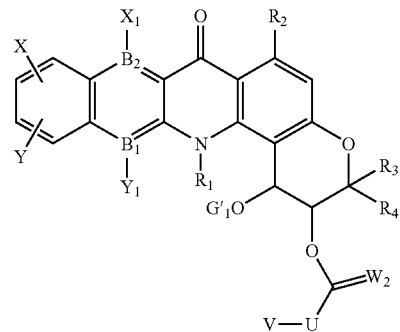
(I/s₂)

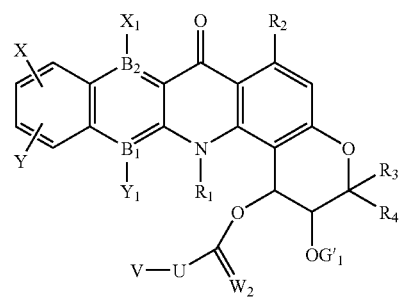
(I/s₃)

wherein X, Y, $X_1$, $Y_1$, $B_1$, $B_2$, $R_1$, $R_2$, $R_3$, $R_4$, $G'_1$, $W_2$, U and V are as defined hereinbefore, 3) or to dehydration conditions in acid medium to yield compounds of formulae (I/t₂) and (I/t₃), particular cases of the compounds of formula (I):

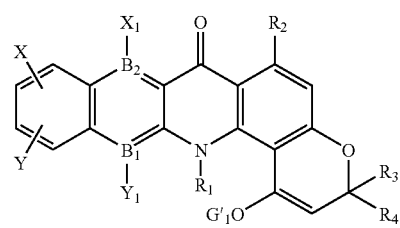
(I/t₂)

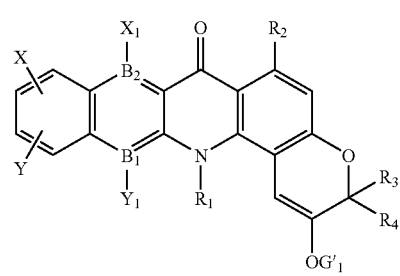
(I/t₃)

wherein X, Y, $X_1$, $Y_1$, $B_1$, $B_2$, $R_1$, $R_2$, $R_3$, $R_4$ and $G'_1$ are as defined hereinbefore, β) or to the action of a compound of formula (XVIII) or (XIX)

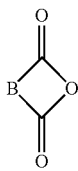

(XVIII)

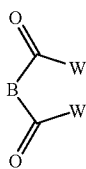

(XIX)

wherein B is as defined for formula (I) and W represents a halogen atom or a hydroxyl group to yield compounds of formula (I/u), a particular case of the compounds of formula (I):

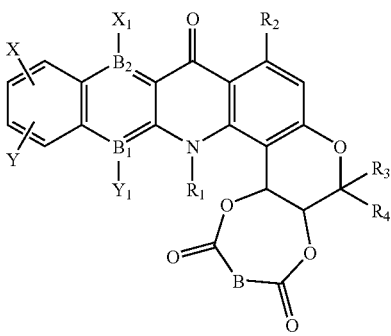

(I/u)

wherein X, Y, $X_1$, $Y_1$, $B_1$, $B_2$, $R_1$, $R_2$, $R_3$, $R_4$ and B are as defined hereinbefore, γ) or to the action of a linear ($C_1$-$C_6$)alkyl dihalide to yield compounds of formula (I/v), a particular case of the compounds of formula (I):

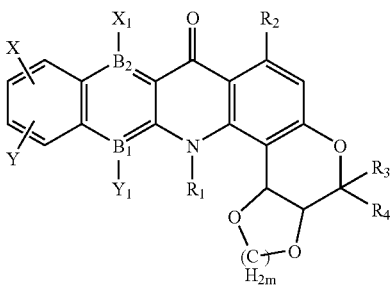

(I/v)

wherein X, Y, $X_1$, $Y_1$, $B_1$, $B_2$, $R_1$, $R_2$, $R_3$ and $R_4$ are as defined hereinbefore and m is as defined for formula (I), ε) or to dehydration conditions in acid medium to yield compounds of formula (I/w), a particular case of the compounds of formula (I):

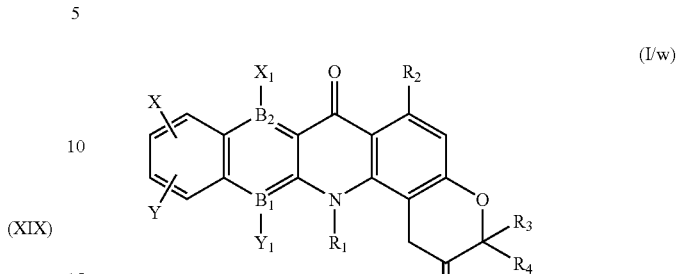

(I/w)

wherein X, Y, $X_1$, $Y_1$, $B_1$, $B_2$, $R_1$, $R_2$, $R_3$ and $R_4$ are as defined hereinbefore, which compounds of formula (I/w) are, if desired, reduced in the presence of $NaBH_4$ to yield compounds of formula (I/x), a particular case of the compounds of formula (I):

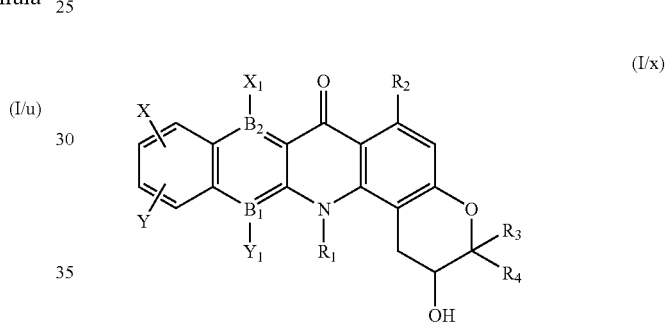

(I/x)

wherein X, Y, $X_1$, $Y_1$, $B_1$, $B_2$, $R_1$, $R_2$, $R_3$ and $R_4$ are as defined hereinbefore, d) or to the action of a peracid or of dimethyl dioxirane to yield compounds of formula (I/y), a particular case of the compounds of formula (I):

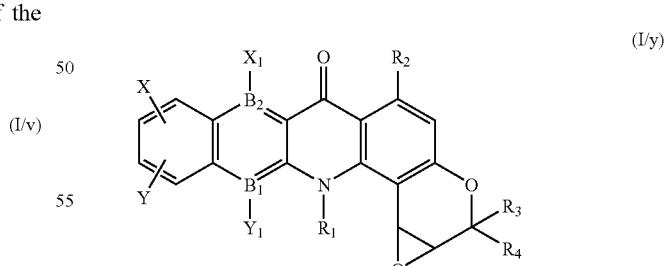

(I/y)

wherein X, Y, $X_1$, $Y_1$, $B_1$, $B_2$, $R_1$, $R_2$, $R_3$ and $R_4$ are as defined hereinbefore, which compounds of formula (I/y) are, if desired, treated with ammonia or a primary or secondary amine to yield compounds of formulae (I/$z_1$) and (I/$z_2$), particular cases of the compounds of formula (I):

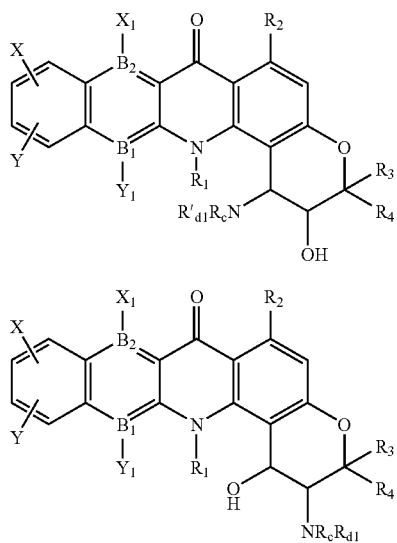

(I/z₁)

(I/z₂)

wherein X, Y, X₁, Y₁, B₁, B₂, R₁, R₂, R₃ and R₄ are as defined hereinbefore, $R_c$ is as defined for formula (I) and $R_{d1}$ represents a group selected from $R_d$, —C(W₂)—U—V, —C(W₂)—W₃-T₁, —S(O)$_n$—W₃-T₁ and —S(O)$_n$-T₁ wherein $R_d$, W₂, W₃, U, V and T₁ are as defined hereinbefore, which compounds of formulae (I/z₁) and (I/z₂) may be subjected α) either, when $R_c$ and $R_{d1}$ represent a hydrogen atom, to the action of a compound of formula (XIII) as defined hereinbefore to yield compounds of formulae (I/aa₁) and (I/aa₂), particular cases of the compounds of formula (I):

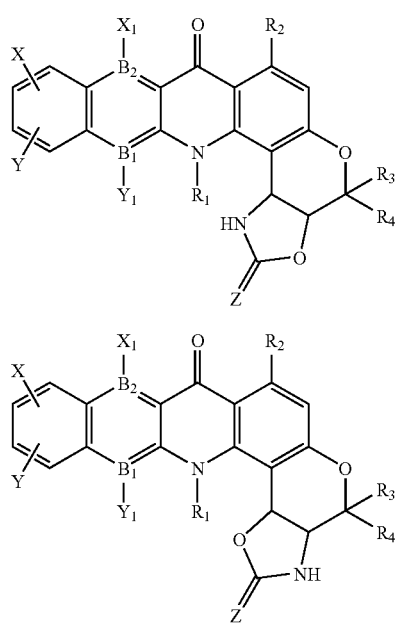

(I/aa₁)

(I/aa₂)

wherein X, Y, X₁, Y₁, B₁, B₂, R₁, R₂, R₃, R₄ and Z are as defined hereinbefore,

β) or to the action of a compound of formula (XIX) as defined hereinbefore to yield compounds of formulae (I/ab₁) and (I/ab₂), particular cases of the compounds of formula (I):

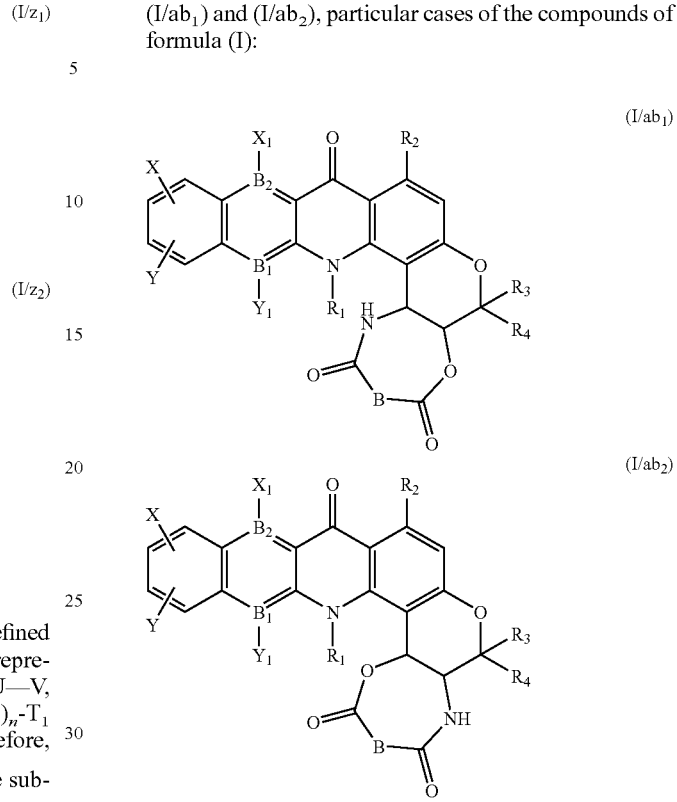

(I/ab₁)

(I/ab₂)

wherein X, Y, X₁, Y₁, B₁, B₂, R₁, R₂, R₃, R₄ and B are as defined hereinbefore,

γ) or to the action of a compound of formula (XVI) as defined hereinbefore to yield compounds of formulae (I/ac₁) and (I/ac₂), particular cases of the compounds of formula (I):

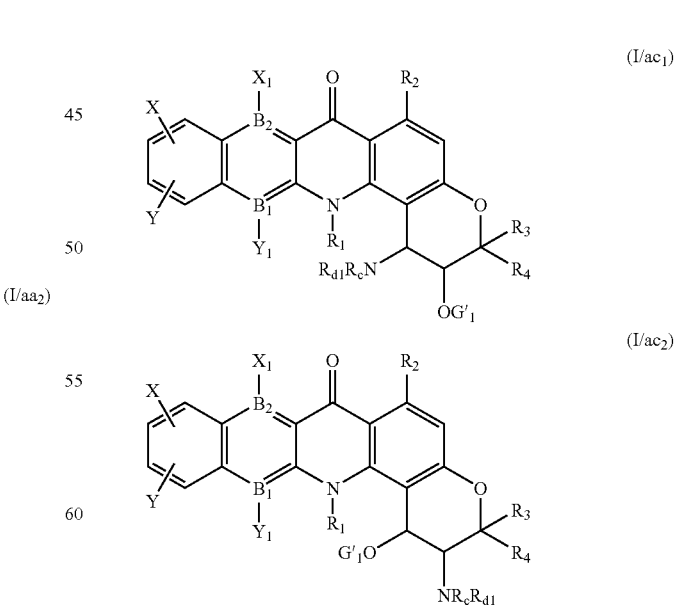

(I/ac₁)

(I/ac₂)

wherein X, Y, X₁, Y₁, B₁, B₂, R₁, R₂, R₃, R₄, $R_c$, $R_{d1}$ and G′₁ are as defined hereinbefore, δ) or to the action of triphenylphosphine dibromide in the presence of triethylamine to yield compounds of formula (I/ad), a particular case of the compounds of formula (I):

(I/ad)

wherein X, Y, $X_1$, $Y_1$, $B_1$, $B_2$, $R_1$, $R_2$, $R_3$, $R_4$ and $R_{d1}$ are as defined hereinbefore, ε) or to the action of $NaN_3$ in the presence of hydrogen peroxide, followed by a reduction step, to yield compounds of formula (I/ae), a particular case of the compounds of formula (I):

(I/ae)

wherein X, Y, $X_1$, $Y_1$, $B_1$, $B_2$, $R_1$, $R_2$, $R_3$ and $R_4$ are as defined hereinbefore, which compounds of formula (I/ae) are, if desired, subjected
1) either to the action of carbon dioxide in the presence of diphenyl phosphite to yield compounds of formula (I/af), a particular case of the compounds of formula (I):

(I/af)

wherein X, Y, $X_1$, $Y_1$, $B_1$, $B_2$, $R_1$, $R_2$, $R_3$ and $R_4$ are as defined hereinbefore,
2) or to the action of a compound of formula (XVI) as defined hereinbefore to yield compounds of formulae (I/ag$_1$), (I/ag$_2$) and (I/ag$_3$), a particular case of the compounds of formula (I):

(I/ag$_1$)

(I/ag$_2$)

(I/ag$_3$)

wherein X, Y, $X_1$, $Y_1$, $B_1$, $B_2$, $R_1$, $R_2$, $R_3$, $R_4$ and $G'_1$ are as defined hereinbefore, the primary amine function of which compounds of formulae (I/ag$_2$) and (I/ag$_3$) is protected by a group for the protection of primary amine groups to yield compounds of formulae (XX/a) and (XX/b), (XX/a)

(XX/b)

wherein X, Y, $X_1$, $Y_1$, $B_1$, $B_2$, $R_1$, $R_2$, $R_3$, $R_4$ and $G'_1$ are as defined hereinbefore and $P_1$ represents a protecting group for primary amine functions, which compounds of formulae (I/ag$_1$) and (XX/a) and (XX/b) are, if desired, subjected to the action of a compound of formula (XXI):

$R_{c1}$-Hal      (XXI)

wherein Hal represents a halogen and $R_{c1}$ represents a group selected from linear or branched ($C_1$-$C_6$)alkyl, aryl and aryl-($C_1$-$C_6$)alkyl in which the alkyl moiety may be linear or branched, and then subjected, in the case of compounds of formulae (XX/a) and (XX/b), to conditions for the deprotection of the primary amine function, to yield compounds of formulae (I/ah$_1$), (I/ah$_2$) and (I/ah$_3$), particular cases of the compounds of formula (I):

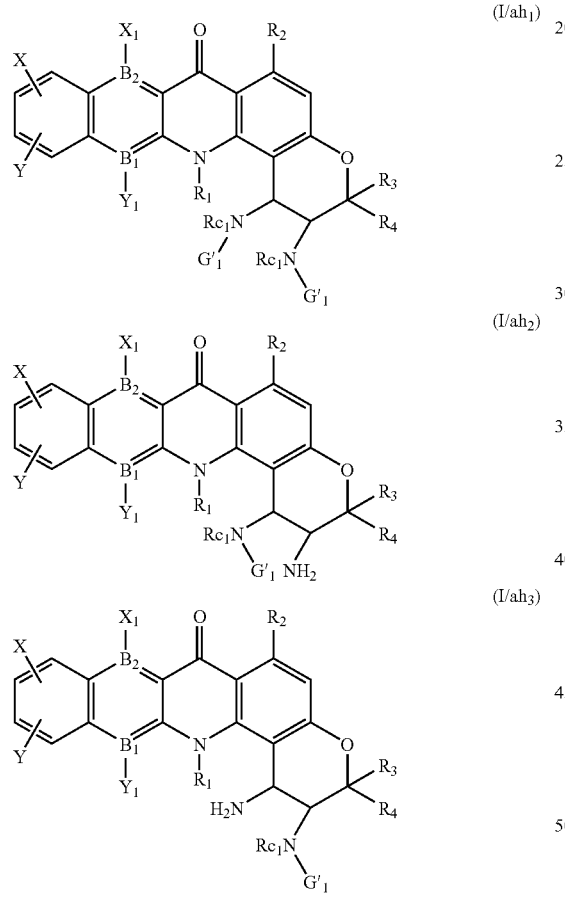

wherein X, Y, $X_1$, $Y_1$, $B_1$, $B_2$, $R_1$, $R_2$, $R_3$, $R_4$, $G'_1$ and $R_{c1}$ are as defined hereinbefore, which compounds of formulae (I/ah$_2$) and (I/ah$_3$) are, if desired, subjected in succession to the action of a compound of formula (XXI) as defined hereinbefore and then to the action of a compound of formula (XXII):

$R_{d1}$-Hal      (XXII)

wherein Hal is as defined hereinbefore and $R_{d1}$ may have the same definitions as $R_{c1}$, to yield compounds of formulae (I/ai$_2$) and (I/ai$_3$), particular cases of the compounds of formula (I):

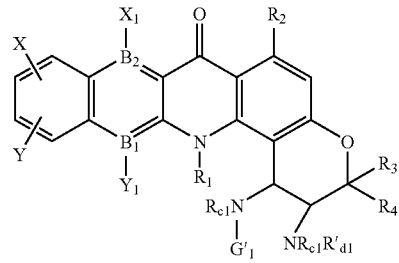

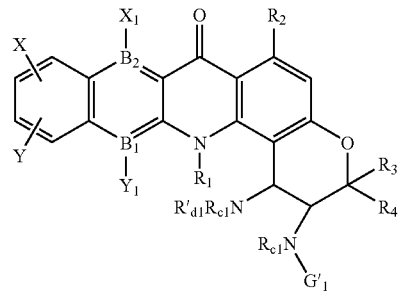

wherein X, Y, $X_1$, $Y_1$, $B_1$, $B_2$, $R_1$, $R_2$, $R_3$, $R_4$, $G'_1$, $R_{c1}$ and $R_{d1}$ are as defined hereinbefore, φ) or to dehydration conditions in acid medium to yield compounds of formulae (I/aj$_2$) and (I/aj$_3$), particular cases of the compounds of formula (I):

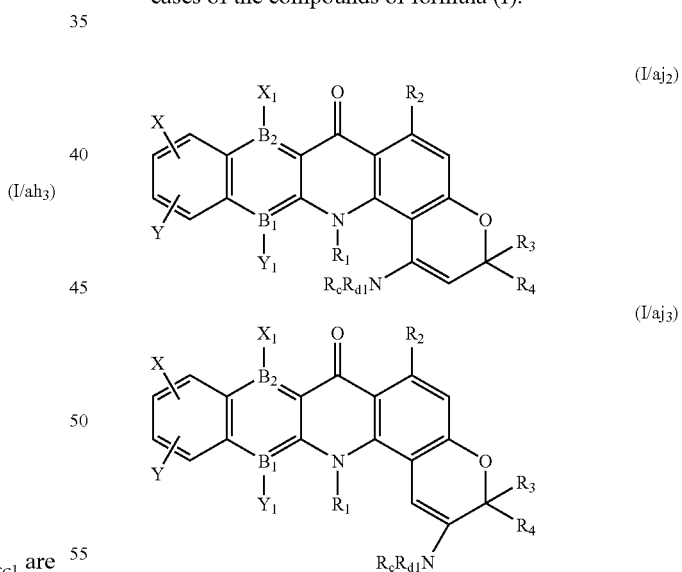

wherein X, Y, $X_1$, $Y_1$, $B_1$, $B_2$, $R_1$, $R_2$, $R_3$, $R_4$, $R_c$ and $R_{d1}$ are as defined hereinbefore, e) or to the action of a compound of formula (XXIII):

Hal-C(W$_2$)-T$_1$      (XXIII)

wherein Hal represents a halogen atom and $W_2$ and $T_1$ are as defined for formula (I) to yield compounds of formula (I/aj), a particular case of the compounds of formula (I):

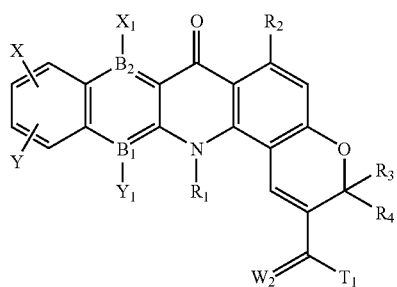

(I/aj)

wherein X, Y, $X_1$, $Y_1$, $B_1$, $B_2$, $R_1$, $R_2$, $R_3$, $R_4$, $W_2$ and $T_1$ are as defined hereinbefore, the compounds (I/a) to (I/aj) constituting the totality of the compounds of the invention, which, if necessary, are purified according to a conventional purification technique, if desired may be separated into their different isomers according to a conventional 5 separation technique and, if desired, are converted into their N-oxides and optionally into addition salts with a pharmaceutically acceptable acid or base.

The compounds of formulae (II), (IV), (IX), (XII), (XIII), (XV), (XVI), (XVII), (XVIII), (XIX), (XXI) and (XXII) are either commercial products or are obtained according to conventional methods of organic synthesis well known to the person skilled in the art.

The compounds of formula (I) have anti-tumour properties of particular interest. They have an excellent cytotoxicity in vitro in relation to cell lines originating from murine and human tumours, owing to a specific blockade of the cell cycle, and are active in vivo in mice in relation to transplantable murine and human tumours. The characteristic properties of the compounds enable them to be used therapeutically as anti-tumour agents.

The present invention relates also to pharmaceutical compositions comprising as active ingredient at least one compound of formula (I), its enantiomers, diastereoisomers, N-oxides or an addition salt thereof with a pharmaceutically acceptable acid or base, on its own or in combination with one or more pharmaceutically acceptable, inert, non-toxic excipients or carriers.

Among the pharmaceutical compositions according to the invention there may be mentioned, more especially, those that are suitable for oral, parenteral (intravenous, intramuscular or subcutaneous), per- or trans-cutaneous, intravaginal, rectal, nasal, perlingual, buccal, ocular or respiratory administration.

The pharmaceutical compositions according to the invention for parenteral injections include especially sterile solutions, which may be aqueous or non-aqueous, dispersions, suspensions or emulsions and also sterile powders for the reconstitution of injectable solutions or dispersions.

The pharmaceutical compositions according to the invention for solid oral administration include especially tablets or dragées, sublingual tablets, sachets, gelatin capsules and granules, and those for liquid oral, nasal, buccal or ocular administration include especially emulsions, solutions, suspensions, drops, syrups and aerosols.

The pharmaceutical compositions for rectal or vaginal administration are preferably suppositories, and those for per- or trans-cutaneous administration include especially powders, aerosols, creams, ointments, gels and patches.

The pharmaceutical compositions mentioned above illustrate the invention but do not limit it in any way.

Among the pharmaceutically acceptable, inert, non-toxic excipients or carriers there may be mentioned, by way of example and without implying any limitation, diluents, solvents, preservatives, wetting agents, emulsifiers, dispersing agents, binders, swelling agents, disintegrators, retardants, lubricants, absorbents, suspending agents, colorants, flavourings etc.

The useful dosage varies according to the age and weight of the patient, the route of administration, the pharmaceutical composition employed, the nature and severity of the disease, and the administration of any associated treatments, and ranges from 0.1 mg to 1000 mg in one or more administrations per day.

The Examples which follow illustrate the invention but do not limit it in any way.

The starting materials used are known products or products prepared according to known procedures. The various preparations result in synthesis intermediates for use in the preparation of the compounds of the invention.

The structure of the compounds described in the Examples and in the Preparations were determined according to customary spectrophotometric techniques (infra-red, nuclear magnetic resonance, mass spectrometry, . . . ).

The melting points were determined using a Kofler hot plate, or a hot plate under a microscope. When the compound is to be found in salt form, the melting point corresponds to that of the salt product.

Preparation 1: 2-Chloro-3-quinolinecarboxylic acid 5 g of 2-chloro-3-quinolinecarboxaldehyde are dissolved in 200 ml of anhydrous dimethylformamide. 96 g of pyridinium dichromate are added in small portions at ambient temperature, a calcium chloride guard is mounted on the flask and the mixture is stirred magnetically for 24 hours. The reaction mixture is diluted with 1 litre of water and extracted with dichloromethane. The combined organic solutions are evaporated to dryness under reduced pressure, in the cold, using a vane pump. Chromatography on silica gel (dichloromethane and then dichloromethane with a methanol gradient of from 0.1 to 2%) allows 1.53 g of the expected product to be isolated.

Mass spectrum (DIC/$NH_3$): m/z=208 (M+H)$^+$. Melting point: 275° C.

Preparation 2: 8-[1,1-Dimethyl-2-propynyl)oxy]-10-hydroxy-6methyl-dibenzo[b,g][1,8]naphthyridin-11-(6H)-one Step A:
2-(3,5-Dimethoxyanilino)-3-quinolinecarboxylic acid A sample of 5 g of the compound of Preparation 1 and 4.93 g of 3,5-dimethoxyaniline are refluxed in 180 ml of anhydrous dimethylformamide in the presence of 5.165 g of anhydrous potassium carbonate and 0.92 g of powdered copper. The reaction mixture is heated at 155° C. for 48 hours under argon. The reaction mixture is evaporated to dryness and the residue is extracted several times with a 1M sodium hydroxide solution. The solution is filtered and then acidified to a pH of 6 using concentrated hydrochloric acid. The precipitate formed is filtered off, washed well with water and dried in air. Chromatography on silica gel (dichloromethane and then dichloromethane with a methanol gradient of from 0.1 to 2%) allows 2.98 g of the expected product to be isolated.

Mass spectrum (ESI-MS): 347 (M+Na)$^+$, 325 (M+H)$^+$. Melting point: 215° C.

Step B: 8,10-Dimethoxydibenzo[b,g][1,8]naphthyridin-11(6H)-one

A mixture of 5.6 g of the compound of the above Step A and 121.8 g of polyphosphoric acid is heated at a temperature of 100° C. for 2 hours. The reaction mixture is poured onto ice and then rendered alkaline to a pH of 6-7 using an aqueous 30% sodium hydroxide solution. The precipitate formed is filtered off, washed with water and dried in air. Chromatography on silica gel (dichloromethane and then dichloromethane with a methanol gradient of from 0.1 to 2%) allows 4.84 g of the expected product to be isolated.

Mass spectrum (DIC/NH$_3$): m/z=307 (M+H)$^+$. Melting point: 279° C.

Step C: 8,10-Dimethoxy-6-methyldibenzo[b,g][1,8]naphthyridin-11(6H)-one 3.89 g of anhydrous potassium hydroxide in powder form are added to a solution of 4.5 g of the compound of the above Step B in 250 ml of anhydrous acetone. The reaction mixture is refluxed for 15 min. at a temperature of 57° C. under argon, and then 10 ml of iodomethane are added three times at intervals of 2 hours. The reaction mixture is refluxed for 3 days. The solvent is evaporated off under reduced pressure. The residue is extracted with water and then filtered. Chromatography on silica gel (dichloromethane and then dichloromethane with a methanol gradient of from 0.1 to 0.5%) allows 3.09 g of the expected product to be isolated.

Mass spectrum (DIC/NH$_3$): m/z=321 (M+H)$^+$. Melting point: 282° C.

Step D: 8,10-Dihydroxy-6-methyldibenzo[b,g][1,8]naphthyridin-11(6H)-one

A sample of 3 g of the compound of the above Step C is dissolved in 150 ml of hydrobromic acid (48% in H$_2$O) and then 50 ml of acetic acid are added. The whole is refluxed for 3 days at 110° C. The reaction mixture is poured onto ice and the precipitate formed is filtered off, washed with water and dried in air. Chromatography on silica gel (dichloromethane and then dichloromethane with a methanol gradient of from 0.1 to 2%) allows 2.35 g of the expected product to be isolated.

Mass spectrum (DIC/NH$_3$): m/z=293 (M+H)$^+$. Melting point: 322° C.

Step E: 8-[(1,1-Dimethyl-2-propynyl)oxy]-10-hydroxy-6-methyldibenzo[b,g][1,8]-naphthyridin-11-(6H)-one A solution of 200 ml of anhydrous dimethylformamide containing 2 g of the compound of the above Step D, 5 g of 3-chloro-3-methyl-1-butyne, 3 g of anhydrous potassium carbonate and 3 g of anhydrous potassium iodide is refluxed for 4 days at 70° C. under nitrogen. The reaction mixture is then poured onto ice and the precipitate is filtered off and washed with water. The aqueous phase is extracted with dichloromethane (4×50 ml). The combined organic phases are dried over anhydrous sodium sulphate, filtered and evaporated to dryness. Chromatography on silica gel (dichloromethane and then a gradient of dichloromethane in methanol of from 0.1% to 0.4%) allows 972.8 mg of the expected product to be isolated.

Mass spectrum (DIC/NH$_3$): m/z=359 (M+H)$^+$. Melting point: 218° C.

Preparation 3: 8-[(1,1-Dimethyl-2-propynyl)oxy]-6-methyldibenzo[b,g][1,8]-naphthyridin-11(6H)-one The product is obtained in accordance with the procedure of Preparation 2 using 3-methoxyaniline instead of 3,5-dimethoxyaniline.

Preparation 4: 7,9-Dihydroxydibenzo[b,g][1,5]naphthyridin-6(11H)-one 3.5 g of 1,3,5-trihydroxybenzene and 62.5 mg of paratoluenesulphonic acid are added to a solution of 5 g of ethyl 3-amino-2-quinolinecarboxylate in 50 ml of heptan-1-ol. The mixture is stirred for 48 hours at reflux using a Dean Stark apparatus and then the reaction mixture is concentrated in vacuo. Chromatography on silica gel (cyclohexane/acetone 90/10) allows 5.2 g of the expected product to be isolated.

Preparation 5: 3-[(1,1-Dimethyl-2-propynyl)oxy]-1-hydroxy-5-methylquino-[2,3-b]quinoxalin-12(5H)-one The product is obtained in accordance with the procedure of Preparation 2 using 3-chloro-2-quinoxalinecarboxylic acid instead of 2-chloro-3-quinolinecarboxylic acid.

EXAMPLE 1

6-Hydroxy-3,3,14-trimethyl-3,14-dihydro-7H-benzo-[b]chromeno-[6,5-g][1,8]naphthyridin-7-one A solution of 500 mg of the compound of Preparation 2 in 170 ml of anhydrous dimethylformamide is maintained at reflux at 130° C. for 2 days under nitrogen. The reaction mixture is evaporated under reduced pressure. Chromatography on silica gel (dichloromethane and then dichloromethane with a methanol gradient of from 0.1 to 0.3%) allows 248.86 mg of the expected product to be isolated.

Mass spectrum (DIC/NH$_3$): m/z=359 (M+H)$^+$. Melting point: 278° C.

EXAMPLE 2

6-Methoxy-3,3,14-trimethyl-3,14-dihydro-7H-benzo[b]chromeno-[6,5-g][1,8]naphthyridin-7-one 840 mg of sodium hydride (50% in liquid paraffin) are added in small portions to a solution, maintained under argon at ambient temperature, of 200 mg of the compound of Example 1 in 40 ml of anhydrous dimethylformamide. The resulting mixture is stirred at ambient temperature and under an inert atmosphere for 15 minutes and then 1.8 ml of iodomethane are added. The reaction mixture is refluxed at 52° C. for 3 hours under argon. Ice is then cautiously added and the precipitate formed is filtered off and dried in air. Chromatography on silica gel (dichloromethane and then dichloromethane with a methanol gradient of from 0.1 to 0.5%) allows 180.26 mg of the expected product to be isolated.

Mass spectrum (DIC/NH$_3$): m/z=373 (M+H)$^+$. Melting point: 270° C.

EXAMPLE 3

(±)-cis-1,2-Dihydroxy-6-methoxy-3,3,14-trimethyl-1,2,3,14-tetrahydro-7H-benzo[b]chromeno[6,5-g][1,8]naphthyridin-7-one A mixture of 500 mg of the compound of Example 2, of osmium tetroxide (2.5%) dissolved in 3.9 ml of 2-methyl-2-propanol and of 626 mg of 4-methylmorpholine N-oxide monohydrate is dissolved in 40 ml of a mixture of 55 ml of t-BuOH-THF—$H_2O$ (10:3:1). The reaction mixture is stirred at ambient temperature for 3 days. A saturated solution of 55 ml of $NaHSO_3$ is then added. After stirring for one hour, the reaction mixture is extracted with water and dichloromethane. The combined organic phases, dried over anhydrous sodium sulphate, are filtered and evaporated to dryness under reduced pressure. Chromatography on silica gel (dichloromethane and then a gradient of methanol in dichloromethane of from 0.1 to 2%) allows 314.29 mg of the expected product to be isolated.

Mass spectrum ($DIC/NH_3$): m/z=407 $(M+H)^+$ Melting point: 298° C.

EXAMPLE 4

(±)-cis-1,2-Diacetoxy-6methoxy-3,3,14-trimethyl-1,2,3,14-tetrahydro-7H-benzo[b]chromeno[6,5-g][1,8]naphthyridin-7-one 200 mg of the compound of Example 3 are added to a previously cooled mixture of 45 ml of anhydrous pyridine, 11 ml of acetic anhydride and 4-dimethylamino-pyridine. The reaction mixture is stirred at ambient temperature for 1 day, with the exclusion of light. The mixture is then poured onto ice, and the precipitate formed is filtered off and washed with water. The aqueous phase is extracted with dichloromethane. The combined organic phases are dried over anhydrous sodium sulphate, filtered, and then evaporated to dryness under reduced pressure. Chromatography on silica gel (dichloromethane and then a gradient of methanol in dichloromethane of from 0.1 to 0.8%) allow 223 mg of the expected product to be isolated.

Mass spectrum ($DIC/NH_3$): m/z=491 $(M+H)^+$ Melting point: 244° C.

EXAMPLE 5

(±)-cis-7-Methoxy-4,4,15-trimethyl-15,15c-dihydro-4H-benzo[b][1,3]-dioxolo[4',5':3,4]chromeno[6,5-g][1,8]naphthyridin-2,8[3aH]-dione 635.62 mg of N,N'-carbonyldiimidazole are added to a solution of 200 mg of the compound of Example 3 in 90 ml of 2-butanone. The reaction mixture is refluxed for 4 days under argon and then, after cooling, diluted with an aqueous 5% $Na_2CO_3$ solution (15 ml) and extracted with ethyl acetate. The organic solutions are combined, dried over anhydrous sodium sulphate, filtered and then evaporated to dryness under reduced pressure. Chromatography on silica gel (dichloromethane and then a gradient of methanol in dichloromethane of from 0.1 to 1.5%) allow 78 mg of the expected product to be isolated.

Mass spectrum (ESI-MS): m/z=433 $(M+H)^+$ Melting point: 234° C.

EXAMPLE 6

(±)-cis-1-{[(Dimethylamino)carbonyl]oxy}-6-methoxy-3,3,14-trimethyl-7-oxo-2,3,7,14-tetrahydro-1H-benzo[b]chromeno[6,5-g]-[1,8]naphthyridin-2-yl dimethylcarbamate At −10° C., add a solution of 0.123 mmol of the compound of Example 3 in 4 ml of anhydrous tetrahydrofuran to 0.698 mmol of potassium hydride washed with hexane. After dropwise addition, at −10° C., of 0.327 mmol of N,N-dimethylcarbamoyl chloride, stirring is maintained for 3 hours 30 minutes at ambient temperature. After the addition of 50 ml of ethyl acetate and 10 ml of a saturated $NaHCO_3$ solution, the organic phase is washed with water and dried over magnesium sulphate and then evaporated under reduced pressure to yield the expected product.

EXAMPLE 7

(±)-cis-6-Methoxy-3,3,14-trimethyl-2-{[(4-methylphenyl)sulphonyl]-oxy}-7-oxo-2,3,7,14-tetrahydro-1H-benzo[b]chromeno[6,5g][1,8]-naphthyridin-1-yl 4-methylbenzenesulphonate The product is obtained according to the procedure of Example 6 using tosyl chloride instead of N,N-dimethylcarbamoyl chloride.

EXAMPLE 8

(±)-cis-4-{[1-(Acetyloxy)-6-methoxy-3,3,14-trimethyl-7-oxo-2,3,7,14-tetrahydro-1H-benzo[b]chromeno[6,5-g][1,8naphthyridin-2-yl]oxy}-4-oxobutanoic acid 1.1 equivalents of succinic anhydride and 1 mg of dimethylaminopyridine are added to a solution of 0.5 mmol of the compound of Example 3 in 3 ml of anhydrous pyridine. Stir for 2 days and in darkness at ambient temperature, then add 25 ml of acetic anhydride and stir for a further 48 hours before concentrating under reduced pressure. Chromatography on silica gel (dichloromethane/acetic acid: 99/1) allows the expected product to be isolated.

EXAMPLE 9

(±)-cis-5-{[(1-(Acetyloxy)-6-methoxy-3,3,14-trimethyl-7-oxo-(2,3,7,14-tetrahydro-1H-benzo[b]chromeno[6,5-g][1,8]naphthyridin-2-yl]oxy}-5-oxopentanoic acid The product is obtained according to the procedure of Example 8 using glutaric anhydride instead of succinic anhydride.

EXAMPLE 10

(±)-cis-1-(Acetyloxy)-6-methoxy-3,3,14-trimethyl-7-oxo-2,3,7,14-tetrahydro-1H-benzo[b]chromeno[6,5-g][1,8]naphthyridin-2-yl [(tert-butoxycarbonyl)amino]acetate Slowly add 0.6 mmol of dicyclohexylcarbodiimide to a solution, at 0° C., of 0.5 mmol of the compound of Example 3 and 0.5 mmol of 2-[(tert-butoxycarbonyl)amino]acetic acid in 10 ml of dimethylformamide. The reaction mixture is maintained at 0° C. for 5 hours and then at ambient temperature for 16 hours. After filtration and evaporation under reduced pressure, the residue is dissolved in 2 ml of anhydrous pyridine, 2 ml of acetic anhydride are added, and stirring is carried out for 48 hours at ambient temperature in darkness. After concentration of the reaction mixture under reduced pressure, chromatography of the residue on silica gel (dichloromethane) allows the expected product to be isolated.

EXAMPLE 11

(±)-cis-1-(Acetyloxy)-6methoxy-3,3,14-trimethyl-7-oxo-2,3,7,14-tetrahydro-1H-benzo[b]chromeno[6,5-g][1,8]naphthyridin-2-yl aminoacetate Add 0.14 µl of iodotrimethylsilane to a solution, at ambient temperature, of 0.1 mmol of the compound of Example 10 in 1 ml of chloroform. The reaction mixture is stirred for 5 min. at ambient temperature and then evaporated to dryness under reduced pressure. Chromatography on silica gel (dichloromethane/methanol:85/15) allows the expected product to be isolated.

EXAMPLE 12

2-Butyryl-6-methoxy-3,3,14-trimethyl-3,14-dihydro-7H-benzo[b]-chromeno[6,5-g][1,8]naphthyridin-7-one A mixture of 0.81 mmol of butyryl chloride and 0.673 mmol of $AlCl_3$ in 2 ml of anhydrous dichloromethane is added in small portions to 0.135 mmol of the product of Example 2 in 2 ml of dichloromethane at 0° C. The reaction mixture is stirred for 4 hours at ambient temperature and then poured into a 10% solution of HCl. Following conventional treatment of the organic phases, and evaporation thereof under reduced pressure, chromatography of the residue on silica gel (dichloromethane/methanol gradient) allows the expected product to be isolated.

EXAMPLE 13

(±)-cis 1-Hydroxy-6-methoxy-3,3,14-trimethyl-7-oxo-2,3,7,14-tetrahydro-1H-benzo[b]chromeno[6,5-g][1,8]naphthyridin-2-yl butyrate Add 2 equivalents of butyryl chloride to a solution of 0.74 mmol of the compound of Example 3 in 7 ml of anhydrous pyridine in the presence of 4-dimethylaminopyridine. Stir at ambient temperature for 72 hours and then add 5 equivalents of butyryl chloride and stir again for 72 hours and then evaporate to dryness. Chromatography on silica gel allows the expected product to be isolated.

EXAMPLE 14

6-Methoxy-3,3,14-trimethyl-7-oxo-7,14-dihydro-3H-benzo[b]chromeno[6,5-g][1,8]naphthyridin-2-yl butyrate Add 4 drops of a 10% solution of HCl to a solution of 0.29 mmol of the compound of Example 13 in 6 ml of dichloromethane. The reaction mixture is stirred for 3 days at ambient temperature and then dried and concentrated under reduced pressure. Chromatography of the residue on silica gel (dichloromethane/methanol gradient) allows the expected product to be isolated.

EXAMPLE 15

2-Hydroxy-6-methoxy-3,3,14-trimethyl-2,3-dihydro-1H-benzo[b]-chromeno[6,5-g][1,8]naphthyridin-1,7(14H)-dione Over the course of 30 minutes, add a suspension of 1.28 g of $KMnO_4$ in 15 ml of water dropwise to a solution of 0.5 g of the product of Example 2 dissolved in 25 ml of acetone. The reaction mixture is stirred at ambient temperature for 8 hours and then, following conventional extraction and treatment, the expected product is isolated by chromatography of the residue on silica gel (dichloromethane/methanol:98/2).

EXAMPLE 16

6-Methoxy-3,3,14-trimethyl-1,7-dioxo-2,3,7,14-tetrahydro-1H-benzo[b]chromeno[6,5-g][1,8]naphthyridin-2-yl acetate The product is obtained according to the procedure of Example 13 starting from the compound of Example 15 and using acetic anhydride instead of butyryl chloride.

EXAMPLE 17

3,3,14-Trimethyl-3,14-dihydro-7H-benzo[b]chromeno[6,5-g][1,8]-naphthyridin-7-one The product is obtained according to the procedure of Example 1 using the compound of Preparation 3 instead of the compound of Preparation 2.

EXAMPLE 18

(±)-cis-1,2-Dihydroxy-3,3,14-trimethyl-1,2,3,14-tetrahydro-7H-benzo[b]chromeno[6,5-g][1,8]naphthyridin-7-one The product is obtained according to the procedure of Example 3 using the compound of Example 17 instead of the compound of Example 2.

EXAMPLE 19

(±)-cis-1,2-(Diacetoxy)-3,3,14-trimethyl-7-oxo-1,2,3,14-tetrahydro-7H-benzo[b]chromeno[6,5-g][1,8]naphthyridin-7-one The product is obtained according to the procedure of Example 4 using the compound of Example 18 instead of the compound of Example 3.

EXAMPLE 20

6-Hydroxy-3,3-dimethyl-3,14-dihydro-7H-benzo[b]chromeno-[5,6-g][1,5]naphthyridin-7-one 2 g of anhydrous potassium carbonate are added to a solution of 2 g of the product of Preparation 4 in 50 ml of anhydrous dimethylformamide under an inert atmosphere. After stirring for 15 minutes at 65° C., 2.4 g of anhydrous potassium iodide and 4.4 g of 3-chloro-3-methyl-1-butyne are added and the reaction mixture is maintained at 65° C. for 24 hours and then at 130° C. for 1 hour 30 minutes. After cooling, the solution is hydrolysed and then extracted with dichloromethane. The combined organic phases are washed with water and then with a 1M potassium hydroxide solution, dried over sodium sulphate and subsequently evaporated. Chromatography on silica gel (cyclohexane/acetone:90/10) allows the expected product to be isolated.

EXAMPLE 21

6-Methoxy-3,3,14-trimethyl-3,14-dihydro-7H-benzo[b]chromeno-[5,6-g][1,5]naphthyridin-7-one The product is obtained according to the procedure of Example 2 using the compound of Example 20.

EXAMPLE 22

(±)-cis-1,2-Dihydroxy-6-methoxy-3,3,14-trimethyl-1,2,3,14-tetrahydro-7H-benzo[b]chromeno[5,6-g][1,5]naphthyridin-7-one The product is obtained according to the procedure of Example 3 using the compound of Example 21.

EXAMPLE 23

(±)-cis-1,2-Diacetyloxy-6-methoxy-3,3,14-trimethyl-1,2,3,14-tetrahydro-7H-benzo[b]chromeno[5,6-g][1,5]naphthyridin-7-one The product is obtained according to the procedure of Example 4 using the compound of Example 22.

EXAMPLE 24

6-Hydroxy-3,3,14-trimethyl-3,14-dihydro-7H-pyrano[2',3':7,8]quino-[2,3-b]quinoxalin-7-one The product is obtained according to the procedure of Example 1 using the compound of Preparation 5 instead of the compound of Preparation 2.

EXAMPLE 25

6-Methoxy-3,3,14-trimethyl-3,14-dihydro-7H-pyrano[2',3':7,8]quino-[2,3-b]quinoxalin-7-one The product is obtained according to the procedure of Example 2 using the compound of Example 24.

EXAMPLE 26

(±)-cis-1,2-Dihydroxy-6-methoxy-3,3,14-trimethyl-1,2,3,14-tetrahydro-7H-pyrano[2',3':7,8]quino[2,3-b]quinoxalin-7-one The product is obtained according to the procedure of Example 3 using the compound of Example 25.

EXAMPLE 27

(±)-cis-1,2-Diacetoxy-6-methoxy-3,3,14-trimethyl-1,2,3,4-tetrahydro-7H-pyrano[2',3':7,8]quino[2,3-b]quinoxalin-7-one The product is obtained according to the procedure of Example 4 using the compound of Example 26.

EXAMPLE 28

(±)-cis-7-Methoxy-4,4,15-trimethyl-15,15c-dihydro-4H-[1,3]dioxolo-[4"5":4',5']pyrano[2',3':7,8]quino[2,3-b]quinoxaline-2,8(3aH)-dione The product is obtained according to the procedure of Example 5 using the compound of Example 26.

PHARMACOLOGICAL STUDY OF THE COMPOUNDS OF THE INVENTION

EXAMPLE 29

In vitro cytotoxicity

Two cell lines were used:
1 murine leukaemia, L1210,
1 human epidermoid carcinoma: KB-3-1

The cells are cultured in RPMI 1640 complete culture medium comprising 10% fcetal calf serum, 2 mM glutamine, 50 units/ml of penicillin, 50 μg/ml of streptomycin and 10 mM Hepes, pH 7.4. The cells are distributed on microplates and are exposed to the cytotoxic compounds. The cells are then incubated for 2 days (L1210) or 4 days (KB-3-1) in an incubator at 37° C. in the presence of 5% $CO_2$. The number of viable cells is then quantified by a colorimetric assay, the tetrazolium microculture assay (Cancer Res. 1987, 47, 939-942).

The results are expressed as $IC_{50}$, the concentration of cytotoxic compound that inhibits the proliferation of the treated cells by 50%. By way of example, the compound of Example 4 exhibits, respectively, an $IC_{50}$ of 0.32 μM in respect of L1210 and of 0.037 μM in respect of KB-3-1.

EXAMPLE 30

Pharmaceutical Composition: Injectable Solution

| | |
|---|---|
| Compound of Example 4 | 10 mg |
| Distilled water for injectable preparations | 25 ml |

The invention claimed is:
1. A compound selected from those of formula (I):

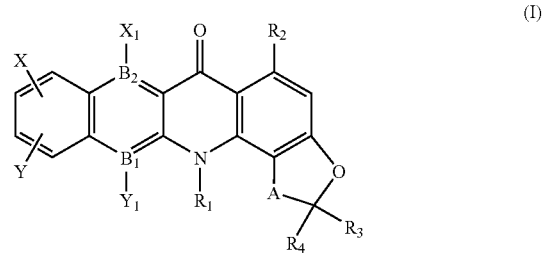

wherein:
$B_1$ and $B_2$, which may be the same or different, represent, independently of one another, carbon or nitrogen, with the proviso that at least one of $B_1$ or $B_2$ represents nitrogen,
X and Y represent hydrogen,
$X_1$ and $Y_1$ represent hydrogen,
it being understood that, when $B_1$ and/or $B_2$ represent nitrogen, $B_1$ and $B_2$ do not carry substituents $Y_1$ and $X_1$, respectively,
$R_1$ represents linear or branched ($C_1$-$C_6$)alkyl,
$R_2$ represents a group selected from hydrogen, linear or branched ($C_1$-$C_6$)alkyl, OR"$_a$; —NR'$_a$R'$_b$; O-T$_a$-OR"$_a$; —NR"$_a$-T$_a$-NR'$_a$R'$_b$; —NR"$_a$-C(O)-T$_a$H; O—C(O)-T$_a$H; —O-T$_a$—NR'$_a$R'$_b$; —NR"$_a$-T$_a$-OR"$_a$; —NR"$_a$-T$_a$-CO$_2$R"$_a$; and —NR"$_a$-C(O)-T$_a$-NR'$_a$R'$_b$,
wherein:
$T_a$ represents linear or branched ($C_1$-$C_6$)alkylene,
R'$_a$ and R'$_b$, which may be the same or different, represent, independently of one another, a group selected from hydrogen, linear or branched ($C_1$-$C_6$)alkyl, or R'$_a$ and R'$_b$, together with the nitrogen atom carrying them, form a monocyclic, 5- to 7-membered heterocycle optionally containing in the cyclic system a second hetero atom selected from oxygen and nitrogen, R″$_a$ represents a group selected from hydrogen and linear or branched (C$_1$-C$_6$)alkyl, R$_3$ and R$_4$, which may be the same or different, represent, independently of one another, hydrogen or a linear or branched (C$_1$-C$_6$)alkyl group, or R$_3$ and R$_4$, together with the carbon atom carrying them, form a monocyclic 3- to 6-membered cyclic group, A represents a group of formula:
—CH(R$_5$)—CH(R$_6$)— wherein:

R$_5$ and R$_6$, which may be the same or different, represent, independently of one another, a group selected from:

hydrogen,

—OR$_c$, NR$_c$R$_d$ and SR$_c$, wherein:

R$_c$ and R$_d$, which may be the same or different, represent, independently of one another, a group selected from hydrogen, linear or branched (C$_1$-C$_6$) alkyl, aryl, aryl-(C$_1$-C$_6$)alkyl in which the alkyl moiety may be linear or branched, or C(O)—R$_e$ wherein R$_e$ represents a group selected from hydrogen, aryl and NR‴$_a$R‴$_b$ wherein R‴$_a$ and R‴$_b$ are identical and represent hydrogen or R‴$_a$ and R‴$_b$, together with the nitrogen atom carrying them, form a monocyclic, 5- to 7-membered heterocycle optionally containing in the cyclic system a second hetero atom selected from oxygen and nitrogen, W$_1$—C(W$_2$)—U—V wherein:

W$_1$ represents oxygen, sulphur or NR$_c$ wherein R$_c$ is as defined hereinbefore, W$_2$ represents oxygen or sulphur, U represents linear or branched (C$_1$-C$_8$)alkylene or linear or branched (C$_2$-C$_8$) alkenylene, V represents a group selected from:
hydrogen,
aryl,
OR$_c$, CO$_2$R$_c$, COR$_c$, CONR'$_a$R'$_b$, NR$_c$R$_d$, N(R$_c$)—CO$_2$R'$_c$, N(R$_c$)—COR'$_c$, wherein R'$_a$, R'$_b$, R$_c$ and R$_d$ are as defined hereinbefore and R'$_c$ represents a group selected from hydrogen, linear or branched (C$_1$-C$_6$)alkyl, aryl, and aryl-(C$_1$-C$_6$) alkyl in which the alkyl moiety may be linear or branched, it being understood that U represents a bond when W$_2$ does not represent an oxygen atom and when simultaneously V does not represent a group selected from hydrogen, aryl and NH$_2$, —W$_1$—C(W$_2$)—W$_3$-T$_1$ wherein:

W$_1$ and W$_2$ are as defined hereinbefore,

W$_3$ represents oxygen, sulphur, or NR$_c$ wherein R$_c$ is as defined hereinbefore, T$_1$ represents a group selected from:
hydrogen,
linear or branched (C$_1$-C$_6$)alkyl,
linear or branched (C$_2$-C$_6$)alkenyl,
aryl,
aryl-(C$_1$-C$_6$)alkyl in which the alkyl moiety may be linear or branched, and
linear or branched (C$_1$-C$_6$)alkylene or linear or branched (C$_2$-C$_6$)alkenylene, each being substituted by a group selected from OR$_c$ and NR'$_a$R'$_b$ wherein R$_c$, R'$_a$ and R'$_b$ are as defined hereinbefore, —W$_1$—S(O)$_n$—W$_3$-T$_1$ wherein:

W$_1$, W$_3$ and T$_1$ are as defined hereinbefore, n represents an integer from 1 and 2, W$_1$-S(O)$_n$-T$_1$ wherein W$_1$, T$_1$ and n are as defined hereinbefore, —C(W$_2$)-T$_1$ wherein W$_2$ and T$_1$ are as defined hereinbefore, or R$_5$ and R$_6$, together form a group selected from:

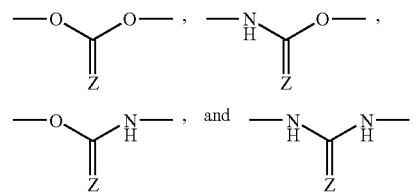

wherein Z represents oxygen or sulphur;

—O—(CH$_2$)$_m$—O— wherein m represents an integer of from 1 to 4 inclusive; and

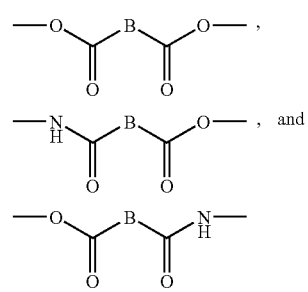

wherein B represents a single bond, linear or branched (C$_1$-C$_6$)alkylene or linear or branched (C$_2$-C$_6$)alkenylene;

or R$_5$ and R$_6$, together with the carbon atoms carrying them, form oxirane or aziridine, optionally substituted on the nitrogen atom by a linear or branched (C$_1$-C$_6$) alkyl, and addition salts thereof with a pharmaceutically acceptable acid or base, it being understood that:

"aryl" may be "phenyl" or "naphthyl" each of those groups being optionally substituted by one or more, identical or different, substituents selected from linear or branched (C$_1$-C$_6$) alkyl, linear or branched (C$_2$-C$_6$)alkenyl, hydroxy, halogen, carboxy, nitro, amino, linear or branched (C$_1$-C$_6$)alkylamino or (C$_1$-C$_6$)dialkylamino wherein each alkyl moiety may be linear or branched, linear or branched (C$_1$-C$_6$)alkoxy, linear or branched (C$_1$-C$_6$) acyl and linear or branched (C$_1$-C$_6$)alkylcarbonyloxy.

2. A compound of claim 1, wherein the compound is selected from those of formula (IA):

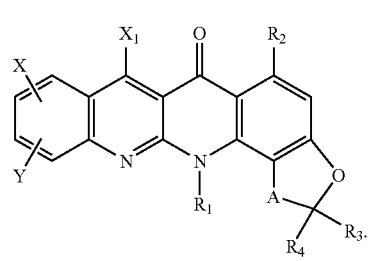

3. A compound of claim 1, wherein the compound is selected from those of formula (IB):

4. A compound of claim 1, wherein the compound is selected from those of formula (IC):

5. A compound of claim 1, wherein the compound is selected from those of formula (ID):

6. A compound of claim 1, wherein the compound is selected from those of formula (IE):

7. A compound of claim 1, wherein the compound is selected from those of formula (IF):

8. A compound of claim 1, wherein the compound is selected from those of formulae (IB), (ID) and (IF), wherein $R_5$ and $R_6$ are identical and represent a group of formula —$OR_c$ or $W_1$—$C(W_2)$—U—V or $R_5$ and $R_6$ together form

9. A compound of claim 1, wherein the compound is selected from those of formulae (IB), (ID) and (IF), wherein $R_5$ and $R_6$ are identical and represent —$OR_c$, wherein $R_c$ represents hydrogen or linear or branched ($C_1$-$C_6$)alkyl.

10. A compound of claim 1, wherein the compound is selected from those of formulae (IB), (ID) and (IF), wherein $R_5$ and $R_6$ are identical and represent $W_1$—$C(W_2)$—U—V, wherein $W_1$ and $W_2$ represent oxygen, U represents linear or branched ($C_1$-$C_6$)alkylene and V represents hydrogen.

11. A compound of claim 1, wherein the compound is selected from those of formulae (IB), (ID) and (IF) wherein $R_5$ and $R_6$ together form wherein Z represents oxygen.

12. A compound of claim 1, wherein $R_3$ and $R_4$ represent linear or branched ($C_1$-$C_6$)alkyl.

13. A compound of claim 1, wherein $R_2$ represents —$OR''_a$.

14. A compound of claim 1, wherein $R_2$ represents —$OR''_a$ wherein $R''_a$ represents linear or branched ($C_1$-$C_6$)alkyl.

15. A compound of claim 14, wherein $R''_a$ represents methyl.

16. A compound of claim 1, wherein X and Y represent hydrogen and one of $X_1$ and $Y_1$ represents hydrogen.

17. A compound of claim 1 which is selected from:
- (±)-cis-1,2-dihydroxy-6-methoxy-3,3,14-trimethyl-1,2,3,14-tetrahydro-7H-benzo[b]-chromeno[6,5-g][1,8]naphthyridin-7-one,
- (±)-cis-1,2-diacetoxy-6-methoxy-3,3,14-trimethyl-1,2,3,14-tetrahydro-7H-benzo[b]-chromeno[6,5-g][1,8]naphthyridin-7-one, and
- (±)-cis-7-methoxy-4,4,15-trimethyl-15,15c-dihydro-4H-benzo[b][1,3]dioxolo-[4',5': 3,4]chromeno[6,5-g][1,8]naphthyridine-2,8(3aH)-dione.

18. A method for treating a living animal body, including a human, afflicted with a condition selected from leukemia and epidermoid carcinoma comprising the step of administering to the living animal body, including a human, an amount of a compound of claim 1, which is effective for alleviation of the condition.

19. A pharmaceutical composition comprising as active principle an effective amount of a compound of claim 1, together with one or more pharmaceutically acceptable excipients or vehicle.